United States Patent
Hoeprich et al.

(10) Patent No.: US 9,303,273 B2
(45) Date of Patent: Apr. 5, 2016

(54) NANOLIPOPROTEIN PARTICLES COMPRISING A NATURAL RUBBER BIOSYNTHETIC ENZYME COMPLEX AND RELATED PRODUCTS, METHODS AND SYSTEMS

(71) Applicants: LAWRENCE LIVERMORE NATIONAL SECURITY, LLC, Livermore, CA (US); THE UNITED STATES OF AMERICA, AS REPRESENTED BY THE SECRETARY OF AGRICULTURE, Washington, DC (US)

(72) Inventors: Paul D. Hoeprich, Pleasanton, CA (US); Maureen Whalen, El Cerrito, CA (US)

(73) Assignees: Lawrence Livermore National Security, LLC, Livermore, CA (US); The United States of America, as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/199,973

(22) Filed: Mar. 6, 2014

(65) Prior Publication Data
US 2014/0273142 A1 Sep. 18, 2014

Related U.S. Application Data

(60) Provisional application No. 61/784,288, filed on Mar. 14, 2013.

(51) Int. Cl.
| | | |
|---|---|---|
| C12P 5/00 | (2006.01) | |
| C12N 9/10 | (2006.01) | |
| C12N 9/96 | (2006.01) | |
| C12P 1/00 | (2006.01) | |

(52) U.S. Cl.
CPC ............... *C12P 5/007* (2013.01); *C12N 9/1085* (2013.01); *C12N 9/96* (2013.01); *C12P 1/00* (2013.01); *C12Y 205/0102* (2013.01); *Y02P 20/52* (2015.11)

(58) Field of Classification Search
None
See application file for complete search history.

(56) References Cited

U.S. PATENT DOCUMENTS

| | | | |
|---|---|---|---|
| 4,317,771 | A | 3/1982 | Shiba et al. |
| 5,393,530 | A | 2/1995 | Schneider et al. |
| 7,015,471 | B2 | 3/2006 | Franzen et al. |
| 7,083,958 | B2 | 8/2006 | Sligar et al. |
| 8,183,010 | B2 | 5/2012 | Swartz et al. |

(Continued)

FOREIGN PATENT DOCUMENTS

| | | |
|---|---|---|
| WO | 00/65099 | 2/2000 |
| WO | 02/40501 | 5/2002 |

(Continued)

OTHER PUBLICATIONS

Berthelot et al., Rubber Elongation Factor (REF), a Major Allergen Component in Hevea brasiliensis Latex Has Amyloid Properties., PLoS One (Epub Oct. 25, 2012), vol. 7(10), pp. 1-12.*

(Continued)

*Primary Examiner* — Alexander Kim
(74) *Attorney, Agent, or Firm* — Steinfl & Bruno, LLP

(57) ABSTRACT

Provided herein are nanolipoprotein particles that comprise a biosynthetic enzyme more particularly an enzyme capable of catalyzing rubber or other rubbers polymerization, and related assemblies, devices, methods and systems.

15 Claims, 4 Drawing Sheets

(56) References Cited

U.S. PATENT DOCUMENTS

| | | |
|---|---|---|
| 2004/0180369 A1 | 9/2004 | Franzen et al. |
| 2005/0182243 A1 | 8/2005 | Sligar et al. |
| 2005/0244414 A1 | 11/2005 | Mundy et al. |
| 2009/0136937 A1 | 5/2009 | Coleman et al. |
| 2009/0192299 A1 | 7/2009 | Chromy et al. |
| 2009/0311276 A1 | 12/2009 | Hoeprich et al. |
| 2010/0203609 A1 | 8/2010 | Yacoby et al. |
| 2011/0059549 A1 | 3/2011 | Coleman et al. |
| 2011/0195450 A1 | 8/2011 | Kudlicki et al. |

FOREIGN PATENT DOCUMENTS

| | | |
|---|---|---|
| WO | 2004/094651 | 4/2004 |
| WO | 2005/070400 | 4/2005 |
| WO | 2006/073419 | 7/2006 |
| WO | 2007/050501 | 3/2007 |
| WO | 2007/038755 | 4/2007 |
| WO | 2008/028206 | 3/2008 |
| WO | 2008/106660 | 4/2008 |

OTHER PUBLICATIONS

Cornish., Biochemistry of natural rubber, a vital raw material, emphasizing biosynthetic rate, molecular weight and compartmentalization, in evolutionarily divergent plant species., Nat. Prod. Rep., (2001), vol. 18, pp. 182-189.*

Cornish et al., Natural Rubber biosynthesis in Plants: Rubber Transferase., Methods in Enzymology (2012), vol. 515, pp. 63-82.*

Branden and Tooze, Introduction to Protein Structure (1999), 2nd edition, Garland Science Publisher, pp. 3-12.*

Guo et al., Protein tolerance to random amino acid change, 2004, Proc. Natl. Acad. Sci. USA 101: 9205-9210.*

Lazar et al., Transforming Growth Factor α: Mutation of Aspartic Acid 47 and Leucine 48 Results in Different Biological Activity, 1988, Mol. Cell. Biol. 8:1247-1252.*

Hill et al., Functional Analysis of conserved Histidines in ADP-Glucose Pyrophosphorylase from *Escherichia coli*, 1998, Biochem. Biophys. Res. Comm. 244:573-577.*

Wacey et al., Disentangling the perturbational effects of amino acid substitutions in the DNA-binding domain of p53., Hum Genet, 1999, vol. 104, pp. 15-22.*

Unger et al., The Genetic Algorithm approach to Protein Structure Prediction, Structure and Bonding (2004), vol. 110, pp. 153-175.*

Lluis et al., Selection Protein engineering methods applied to membrane protein targets (2013), vol. 26(2), pp. 91-100.*

Gursky, O., Ranjana, and Gantz, D. L. (2002) Complex of human apolipoprotein C-1 with phospholipid: thermodynamic or kinetic stability? *Biochemistry* 41, p. 7373-84.

Hamdy, S., Haddadi, A., Somayaji, V., Ruan, D. And Samuel, J. (2007). Pharmaceutical analysis of synthetic lipid A-based vaccine adjuvants in poly (d,l-lactic-co-glycolic acid) nanoparticle formulations. *Journal of Pharmaceutical and Biomedical Analysis* 44:914-923.

Hartmuth Kolb and Barry Sharpless (2003) "The growing impact of click chemistry on drug discovery" *Drug Discov. Today* 8:1128-1137.

Hedderich, R. Energy-converting [NiFe] Hydrogenases from archaea and Extromohiles: Ancestors of Complex I *Journal of Bioenergetics and Biomembranes* (2004), 36, (I), 65-75.

Hein, C.D., Liu, X-M, and Wang, D. (2008). Click Chemistry, A Powerful Tool for Pharmaceutical Sciences. Pharmaceutical Research, vol. 25, No. 10:2216-2230.

Hiraishi, Tomohiro; Taguchi, Seiichi "Enzyme-catalyzed Synthesis and Degradation of Biopolymers" Mini-Reviews in Organic Chemistry, vol. 6, No. 1, Feb. (2009), pp. 44-54(11) Bentham Science Publishers.

Ho, D.; Chu, B.; Lee, H.; Brooks, E. K.; Kuo, K.; Montemagno, C. D. "Fabrication of biomolecule-copolymer hybrid nanovesicles as energy conversion systems" *Nanotechnology* (2005), 16, (12), 3120-3132.

Huleatt, J.W., Nakaara, V., Desaia, P., Huanga, Y., Hewitta, D., Jacobs, A., Tanga, J., McDonald, W., Song, L., Evans, R.K., Umlauf, S., Tussey, L., and Powell, T.J. (2008). Potent immunogenicity and efficacy of a universal influenza vaccine candidate comprising a recombinant fusion protein linking influenza M2e to the TLR5 ligand flagellin *Vaccine* 26:201-214.

Ueda et al. Induction of tumor necrosis factor-a in solid tumor region by the orally administered synthetic muramyl dipeptide analogue, romurtide (2001) *Int'l Immunopharm.* 1:97-104.

Jayaraman, S., Gantz, D., and Gursky, 0. (2005) Structural basis for thermal stability of human low-density lipoprotein. *Biochemistry* 44, p. 3965-71.

Jasanada et al., (1996) "Indium-111 Labeling of Low Density Lipoproteins with the DTPA-BIS(Stearylamide): Evaluation as a potential Readio pharmaceutical for Tumor Localization" *Bioconj. Chem.* 7(1): 72-81.

Eberly, J.E. And R.L. Ely Thermotolerant Hydrogenases: Biological Diversity, Properites and Biotechnical Applications *Critical Reviews in Microbiology*, 34:117-130, (2008).

Jonas, A. Reconstitution of high-density lipoproteins *Methods Enzymol.* (1986), 128, 553-82.

Kalmbach, R., Chizhov, I., Schumacher, M. C., Friedrich, T., Bamberg, E., and Engelhard, M. (2007) Functional cell-free synthesis of a seven helix membrane protein: in situ insertion of bacteriorhodopsin into liposomes. *J Mol Bio*/371, p. 639-648.

Katzen et al. Insertion of Membrane Proteins into Discoidal Membranes using a Cellfree Protein Expression Approach (2008) *J. Proteome Res.* vol. 7, 3536-3542.

Kim et al., Gold Nanoparticle-Enhanced Secondary Ion Mass Spectrometry Imaging of Peptides on Self-Assembled Monolayers, *Anal. Chem.*, 78 (2006), p. 1913-1920.

Klammt, C., Lohr, F., Schafer, B., Haase, W., Dotsch, V., Rutetjans, H., Glaubitz, C.,and Bernhard, F. (2004) High level cell-free expression and specific labeling of integral membrane proteins. *Eur J Biochem* 271, p. 568-580.

Klammt, C., Schwarz, D., Fendler, K., Haase, W., Dotsch, V., and Bernhard, F. (2005) Evaluation of detergents for the soluble expression of alpha-helical and beta-barrel-type integral membrane proteins by a preparative scale individual cell-free expression system. *Febs J.* 272, p. 6024-6038.

Klammt, C., Schwarz, D., Lohr, F., Schneider, B., Dotsch, V., and Bernhard, F. (2006) Cell-free expression as an emerging technique for the large scale production of integral membrane protein. *Febs J* 273, p. 4141-4153.

Konishi, E., and P. W. Mason. (1993). Proper maturation of the Japanese encephalitis virus envelope glycoprotein requires cosynthesis with the premembrane protein. *J Virol* 67:1672-5.

Kovacs, K. L.; Maroti, G.; Rakhely, G. "A novel approach for biohydrogen production" *International Journal of Hydrogen Energy* (2006), 31, (11), 1460-1468.

Lechene et al., High-resolution quantitative imaging of mammalian and bacterial cells using stable isotope mass spectrometry *Journal of biology* 5, 20 (2006).

Leitz, A. J.; , T. H.; Basnakov, A. N.; Springer, B. A,; Sligar, S. G. Functional reconstitution of Beta2-adrenergic receptors utilizing selfassembling Nanodisc technology Biotechniques (2006), 40, (5), 601-612.

Lu, B., Morrow, J. A., and Weisgraber, K. H. (2000) Conformational reorganization of the four-helix bundle of human apolipoprotein E in binding to phospholipid. *J Biol Chem* 275, p. 20775-81.

Ludwig et al., ARB: a software environment for sequence data. *Nucl. Acids Res.* 32, 1363-71 (2004).

Manefield, A. S. Whiteley, R. I. Griffiths, M. J. Bailey, RNA Stable Isotope Probing, a Novel Means of Linking Microbial Community Function to Phylogeny *Appl. Environ. Microbiol.* 68, 5367 (2002).

Martin and B.F. Cravatt (2009) "Large-scale profiling of protein palmitoylation in mammalian cells" *Nat. Methods* 6:135-138.

Masquelier M. et al., (1986) "Low-Density lipoprotein as a carries of antitumoral drugs: In vivo fate of drug-human low-density lipoprotein complexes in mice." *Cancer Research , American Association for Cancer Research* 46(1): 3842-3847.

(56) References Cited

OTHER PUBLICATIONS

McGall et al. "The Efficiency of Light-Directed Synthesis of DNA Arrays on Glass Substrates" *J. Amer. Che. Soc.* (1997),119:5081-5090.
Meyer. J., et al., Fe/Fe hydrogenases and their evolution: a genomic perspective. *Cell. Mol. Life. Sci.* 64 (2007) 1063-1084.
Morrow, J. A., Arnold, K. S., and Weisgraber, K. H. (1999) Functional characterization of apolipoprotein E isoforms overexpressed in *Escherichia coli. Protein Expr Purif* 16, p. 224-230.
Moses et al., Detection of DNA hybridization on indium tin oxide surfaces. *Sensors and Actuators B*, 125 (2007) 574-580.
Nath, A,; Atkins, W. M.; Sligar, S. G. Applications of Phospholipid Bilayer Nanodiscs in the Study of Membranes and Membrane Proteins*Biochemistry* (2007),46, (8), 2059-2069.
N. O. Fischer, Craig D. Blanchette, Brett A. Chromy, Edward A. Kuhn, Brent W. Segelke, Michele Corzett, Graham Bench, Peter W. Mason, and Paul D. Hoeprich (2009) "Immobilization of His-Tagged Proteins on Nickel-Chelating Nanolipoprotein Particles" *Bioconjugate Chemistry* 20:460-465.
North P. and Fleischer S. Alteration of Synaptic Membrane Cholestorl/Phosphol Ratio Using a Lipid Transfer Protein (1983) *J. Biol. Chem.* vol. 258, No. 2. pp. 1242-1253.
Ohya; T. Koyama, (2001). "Biosynthesis of Natural Rubber and Other Natural Polyisoprenoids". *Biopolymers Polyisoprenoids*. 2.1 p. 73-81.
Ouverney, J. A. Fuhrman, Combined Microautoradiography—16S rRNA Probe Technique for Determination of Radioisotope Uptake by Specific Microbial Cell Types in Situ *Appl. Environ. Microbiol.* 65, 1746 (Apr. 1, 1999).
Parkin, A., Goldet, G. Cavazza, C. Fontecilla-Camps, J., Armstrong, F. J. The Difference a Se Makes? . . .*Am Chem. Soc.* (2008), 13 (40) 13410-13416.
Pasini EM et al., In-depth analysis of the membranes and cytosolic proteome of red blood cells (2006) Blood, 108: 791-801.
Persson, et al., (1996) "Topology prediction of membrane proteins." *Protein Science* 5:363-371.
Paterson-Jones, M.G. Gilliland, J. Van Staden, The Biosynthesis of Natural Rubber, *Journal of Plant Physiology*, vol. 136, Issue 3, Jun. (1990), pp. 257-263.
Petrakova, O., E. Volkova, R. Gorchakov, S. Paessler, R. M. Kinney, and I. Frolov. (2005). Noncytopathic replication of Venezuelan equine encephalitis virus and eastern equine encephalitis virus replicons in Mammalian cells. *J Virol* 79:7597-608.
Osada et al. Polymorphonuclear Leukocyte Activation by a Synthetic Muramyl Dipeptide Analog (1982) *Inf. Immun.* 38:848-854.
Ponciano et al. "Transcriptome and gene expression analysis in cold-acclimated guayule (Parthenium argentum) rubber-producing tissue", (2012) *Phytochemistry* 79:57-66.
Radajewski, P. Ineson, N. R. Parekh, J. C. Murrell, Stable-isotope probing as a tool inmicrobial ecology. *Nature* 403, 646 (2000).
Rensen, et al., (2001) "Recombinant Lipoproteins: Lipoprotein-like Lipid particles for drug targeting." *Adv. Drug Delivery Rev.* Elsevier BV, Amsterdam, 47(25):251-276.
Rao, R. S., Visuri, S. R., McBride, M. T., Albala, J. S., Matthews, D. L., and Coleman, M.A. (2004) Comparison of multiplexed techniques for detection of bacterial and viral proteins. *J Proteome Res* 3, p. 736-742.
Sanderson, K. Nature The photon trap (2008), 452, 400-402.
Sapra, R.; Bagratnyan, K.; Adams, M. W. W. A simple energy-conserving system: Proton reduction coupled to proton translocation *Proceedings of the National Academy of Sciences* (2003), 100, (13), 7545-7550.
Sapra, R.; Verhagcn, M. F. J. M.; Adams, M. W. W. Purification and Characterization of a membrane-bound hydrogenase from the hyperthermophilic archeon . . .*Journal of Bacteriology* (2000), 182, (12), 3423-3428.
Schena et al. "Quantitative Monitoring of Gene Expression Patterns with a Complementary DNA Microarray" *Science*, (1995), 270:467-470.

Schmidt et al. "Characterization of rubber particles and rubber chain elongation in Taraxacum koksaghyz." (2010) *BMC Biochemistry* 11:1-11.
Schmitt et al., "Synthesis and Characterization of chelator-lipids for reversible immobilization of engineered proteins at self assembled lipid interfaces", *J. Am. Chem. Soc.* 116: 8485-8491 (1994).
Segelke, B. W., Schafer, J., Coleman, M.A., Lekin, T. P., Toppani, D., Skowronek, K. 1., Kantardjieff, K. A., and Rupp, B. (2004) Laboratory scale structural genomics. *J Struct Funct Genomics* 5, p. 147-157.
Siler et al. "Composition of rubber particles of Hevea brasiliensis, Parthenium argentatum, Ficus elastics and Euphorbia lactiflua indicates unconventional surface structure" (1997) *Plant Physiol. Biochem.* 35:881-889.
Silvius, J.R. (1982) Thermotropic phase transitions of pure lipids in model membranes and their modification by membrane proteins. In Lipid-Protein Interactions (P.C. Jost and O.H. Griffith, Eds.) vol. 2. *New York: Wiley*.
Simon and W.H. Konigsberg (1966) "Chemical modification of hemoglobins: a study of conformation restraint by internal bridging", *Proc Natl Acad Sci U S A.* 56:749.
Singh et al. The micromorphology and protein characterization of rubber particles in Ficus carica, Ficus benghalensis and Hevea brasiliensis*Journal of Experimental Botany* vol. 54, No. 384, pp. 985-992, (2003).
Singh-Gasson et al., Maskless fabrication of light-directed oligonucleotide microarrays using a digital micromirror array*Nat. Biotech.* 17, 974 (1999).
Sonar, S., Marti, T., Rath, P., Fischer, W., Coleman, M., Nilsson, A., Khorana, H. G., and Rothschild, K. J. (1994) A redirected proton pathway in the bacteriorhodopsin mutant Tyr-57-->Asp. Evidence for proton translocation without Schiff base deprotonation. *J Biol Chem* 269, p. 28851-2885.
Sonar, S., Patel, N., Fischer, W., and Rothschild, K. J. (1993) Cell-free synthesis, functional refolding, and spectroscopic characterization of bacteriorhodopsin, an integral membrane protein. *Biochemistry* 32, p. 13777-781.
Stadermann, R. M. Walker, E. Zinner. Nanosims: The Next Generation Ion Probe for the Microanalysis of Extra Terrestrial Material *Meteoritics & Planetary Science* 34, A111-1112 (Jul. 1999).
Sun, X. et al. Membrane-Mimetic Films of Aymmetric Phosphtidylcholine Lipid Bolaamphiphiles. *Langmuir* 2006, 22, 1201-1208.
Terpe (2003) "Overview of tag protein fusions: from molecular and biochemical fundamentals to commercial systems" *Appl Microbiol Biotechnol*, 60:523-533.
Tufteland, M., et al., (2007) "Peptide stabilized amphotericin B nanodisks." *Peptides* 28:741-746.
Uhlík, K. Jecná, M. B. Leigh, M. Macková, T. Macek, DNA-based stable isotope probing: a link between community structure and function. *Sci. Total Environ.* 407, 3611 (2009).
Vignais, P.M., et al., (2007) "Occurrence, classification and biological function of hydrogenases: an overview" *Chem. Rev.* 107:4206-4272.
Vincent, K.A., et al., (2005) "Electrocatalytic hydrogen oxidation by an enzyme at high carbon monoxide or oxygen levels." 102(47): 16951-16954.
Vincent, K. A. et al. "Investigating and Exploiting the Electrocatalytic Properties of Hydrogenases" *Chem. Rev.* 2007 107, 4366-4413.
Wang, S. Link, C.D. Heyes and M.A. EI-Sayed. Comparison of the dynamics of the primary events of bacteriorhodopsin in its trimeric and monomeric states, *Biophys. J.* 83 (2002), pp. 1557-1566.
Weeratna, R.D., McCluskie, M.J., Xu, Y., and Davis, H.L. 2000. CpG DNA induces stronger immune responses with less toxicity than other adjuvants. *Vaccine* 18:1755-62.
Whalen et al Chapter 23 of T.J. Bach and M. Rohmer (eds.) Isoprenoid Synthesis in Plants and Microorganisms: New Concepts and Experimental Approaches, *Springer Science + Business Media New York*, 2013.
Widman, D. G., T. Ishikawa, R. Fayzulin, N. Bourne, and P. W. Mason. 2008. Construction and characterization of a second-genera-

(56) References Cited

OTHER PUBLICATIONS tion pseudoinfectious West Nile virus vaccine propagated using a new cultivation system. *Vaccine* 26:2762-2771.
Wientzek, M., Kay, C. M., Oikawa, K., and Ryan, R. 0. (1994) Binding of insect apolipophorin III to dimyristoylphosphatidylcholine vesicles. Evidence for a conformational change. *J Biol Chem* 269, p. 4605-4612.
Woodward, J.; Mattingly, S. M.; Danson, M.; Hough, D.; Ward, N.; Adams, M. In vitro hydrogen production by glucose dehydrogenase and hydrogenase *Nature Biotechnology* 1996, 14,872-874.
Woodward, J., et al., (2000) "Enzymatic production of biohydrogen." *Nature* 405:1014-1015.
Wuu, J., et al., (2008) "High yield cell-free production of integral membrane proteins without refolding or detergents." *Biochimica et Biophysica Acta* 1778:1237-1250.
Xie, W., et al., (2008) "Initiation of rubber biosynthesis: In vitro comparisons of benzophenone-modified diphosphate analogues in three rubber-producing species." *Phytochemistry* 69:2539-2545.
Zhang, P.Y-H., et al., (2007) "High-yield hydrogen production from starch and water by a synthetic enzymatic pathway." *PLoS One* 5:e456.
Zhiqiang Pan, Francis Durst, Daniele Werck-Reichhart, Harold W. Gardner, Bilal Camarall, Katrina Cornish, and Ralph A. Backhausi The Major Protein of Guayule Rubber Particles Is a Cytochrome P450. *The journal of Biological Chemistry*, vol. 270, No. 15, Issue of Apr. 14, pp. 8487-8494, 1995.
Advisory Action issued for U.S. Appl. No. 12/118,530, filed May 9, 2008 in the name of Matthew Coleman; mail date: Jun. 6, 2012.
Restriction Requirement issued for U.S. Appl. No. 12/118,530, filed May 9, 2008 in the name of Matthew Coleman; mail date: Sep. 24, 2010.
Restriction Requirement issued for U.S. Appl. No. 12/118,530, filed May 9, 2008 in the name of Matthew Coleman; mail date: Mar. 30, 2011.
Non-Final Office Action issued for U.S. Appl. No. 12/118,530, filed May 9, 2008 in the name of Matthew Coleman; mail date: Aug. 30, 2011.
Final Office Action issued for U.S. Appl. No. 12/118,530, filed May 9, 2008 in the name of Matthew Coleman; mail date: Jan. 25, 2012.
Non-Final Office Action issued for U.S. Appl. No. 12/118,396, filed May 9, 2008 in the name of Matthew Coleman; mail date: Aug. 30, 2011.
Final Office Action issued for U.S. Appl. No. 12/118,396, filed May 9, 2008 in the name of Matthew Coleman; mail date: Jan. 18, 2012.
Advisory Action issued for U.S. Appl. No. 12/118,396, filed May 9, 2008 in the name of Matthew Coleman; mail date: Jun. 7, 2012.
Restriction Requirement issued for U.S. Appl. No. 12/118,396, filed May 9, 2008 in the name of Matthew Coleman; mail date: Mar. 4, 2011.
Restriction Requirement issued for U.S. Appl. No. 12/352,548, filed Jan. 12, 2009 in the name of Brett a. Chromy; mail date: Apr. 25, 2011.
Non-Final Office Action issued for U.S. Appl. No. 12/352,548, filed on Jan. 12, 2009 in the name of Brett A. Chromy; mail date: Sep. 13, 2011.
Notice of Allowance issued for U.S. Appl. No. 12/352,548, filed Jan. 12, 2009 in the name of Brett a. Chromy; mail date: Mar. 12, 2012.
Notice of Allowance issued for U.S. Appl. No. 12/352,548, filed Jan. 12, 2009 in the name of Brett a. Chromy; mail date: Aug. 5, 2014.
Restriction Requirement issued for U.S. Appl. No. 12/469,533, filed May 20, 2009 in the name of Paul D. Hoeprich; mail date: Jun. 7, 2011.
Non-Final Office Action issued for U.S. Appl. No. 12/469,533, filed May 20, 2009 in the name of Paul D. Hoeprich; mail date: Oct. 24, 2011.
Non-Final Office Action issued for U.S. Appl. No. 12/469,533, filed May 20, 2009 in the name of Paul D. Hoeprich; mail date: May 23, 2012.
Final Office Action issued for U.S. Appl. No. 12/469,533, filed May 20, 2009 in the name of Paul D. Hoeprich; mail date: Dec. 4, 2012.

Restriction Requirement issued for U.S. Appl. No. 12/366,476, filed Feb. 5, 2009 in the name of Paul D. Hoeprich Jr.; mail date: Sep. 23, 2011.
Non-Final Office Action issued for U.S. Appl. No. 12/366,476, filed Feb. 5, 2009 in the name of Paul D. Hoeprich Jr.; mail date: Nov. 15, 2011.
Non-Final Office Action issued for U.S. Appl. No. 12/366,476, filed Feb. 5, 2009 in the name of Paul D. Hoeprich Jr; mail date: Apr. 23, 2012.
Final Office Action issued for U.S. Appl. No. 12/366,476, filed Feb. 5, 2009 in the name of Paul D. Hoeprich Jr; mail date: Oct. 16, 2012.
Restriction Requirement issued for U.S. Appl. No. 12/352,472, filed Jan. 12, 2009 in the name of Sarah E Baker; mail date: May 27, 2011.
Non-Final Office Action issued for U.S. Appl. No. 12/352,472, filed Jan. 12, 2009 in the name of Sarah E Baker; mail date: Sep. 22, 2011.
Final Office Action issued for U.S. Appl. No. 12/352,472, filed Jan. 12, 2009 in the name of Sarah E Baker; mail date: Jun. 7, 2012.
Non-Final Office Action issued for U.S. Appl. No. 12/352,472, filed Jan. 12, 2009 in the name of Sarah E Baker; mail date: Oct. 2, 2013.
Restriction Requirement issued for U.S. Appl. No. 12/604,362, filed Oct. 22, 2009 in the name of Paul D. Hoeprich; mail date: Jan. 11, 2012.
Non-Final Office Action issued for U.S. Appl. No. 12/604,362, filed Oct. 22, 2009 in the name of Paul D. Hoeprich; mail date: May 7, 2012.
Final Office Action issued for U.S. Appl. No. 12/604,362, filed Oct. 22, 2009 in the name of Paul D. Hoeprich; mail date: Dec. 4, 2012.
Restriction Requirement issued for U.S. Appl. No. 13/023,468, filed Feb. 8, 2011 in the name of Jennifer Pett-ridge; mail date: Aug. 31, 2012.
Non-Final Office Action issued for U.S. Appl. No. 13/023,468, filed Feb. 8, 2011 in the name of Jennifer Pett-ridge; mail date: Oct. 26, 2012.
International Search Report for PCT/US2008/063307 filed on May 9, 2008 in the name of Lawrence Livermore National Security mail date: Oct. 29, 2008.
Written Opinion for PCT/US2008/063307 filed on May 9, 2008 in the name of Lawrence Livermore National Security mail date: Oct. 29, 2008.
International Search Report for PCT/US2009/044722 filed on May 20, 2009 in the name of Lawrence Livermore National Security mail date: Oct. 28, 2010.
Written Opinion for PCT/US2009/044722 filed on May 20, 2009 in the name of Lawrence Livermore National Security mail date: Oct. 28, 2010.
International Search Report for PCT/US2009/033193 filed Feb. 5, 2009 in the name of Lawrence Livermore National Security mail date: Sep. 30, 2009.
Written Opinion for PCT/US2009/033193 filed on Feb. 5, 2009 in the name of Lawrence Livermore National Security mail date: Sep. 30, 2009.
Yoon et al. "Three-Dimensional Graphene Nano-Networks with High Quality and Mass Production Capability via Precursor—Assisted Chemical Vapor Deposition" Scientific Reports (2013) 3:1788, 1-8.
Peters-Libeau et al. "Model of Biologically Active Apolipoprotein E Bound to Dipalmitoylphosphatidylcholine" The Journal of Biological Chemistry vol. 281, No. 2, pp. 1073-1079, (2006).
Whorton M. et al. "A monomeric G protein-coupled receptor isolated in a high-density lipoprotein particle efficiently activates its G protein" Proc Natl Acad Sci USA 104, 7682-7.
Non-Final Office Action issued for U.S. Appl. No. 12/118,396 in the name of Lawrence Livermore National Security; mail date: Jul. 22, 2014.
Rusinol et al. "In Vitro Reconstitution of Assembly of ApolipoproteinB48-containing Lipoproteins", Journal of Biological Chemistry vol. 272, No. 12, Issue of Mar. 21, pp. 8019-8025, (1997).
Walter et al. "Preparation of Microsomal Membranes for Cotranslational Protein Translocation" (1983) Methods Enzymol. 96, 84-93.
Non-Final Office Action issued for U.S. Appl. No. 12/352,472 in the name of Lawrence Livermore National Security; mail date: Dec. 26, 2014.

(56) References Cited

OTHER PUBLICATIONS

Baas, B.J., et al. "Homotropic cooperativity of monomeric cytochrome P450 EA4 in a nanoscale native bilayer environment" Archives of Biochemistry and Biophysics (2004) 430: 218-228.

Notice of Allowance issued for U.S. Appl. No. 12/604,362 in the name of Lawrence Livermore National Security; mail date: Oct. 30, 2014.

DeSantis et al., Greengenes, a Chimera-Checked 16S Rrna Gene Database and Workbench Compatible with ARB. Appl. Environ. Microbiol. 72, 5069-5072 (2006).

Fischer et al. "Conjugation to Nickel-Chelating Nanolipoprotein Particles Increases the Potency and Efficacy of Subunit Vaccines to Prevent West Nile Encephalitis" Bioconjugate Chemistry 2010, 21: pp. 1018-1022.

Vuorilehto et al., "Indirect electrochemical reduction of nicotinamide coenzymes", Bioelectrochemistry 65 (2004). pp. 1-7.

Lam, K. S. et al., "Application of combinatorial library methods in cancer research and drug discovery" Anticancer Drug Des. (1997) pp. 145-167.

Cruz, F., et al. "Kinetic properties of recombinant MAO-A on incorporation into phospholipid nanodisks" J Neural Transm 114, 699-702. (2007).

R. A. Sperling, et al. "Surface modification, functionalization and bioconjugation of colloidal inorganic nanoparticles". Phil. Trans. R. Soc. A (2010) vol. 368 No. 1915 pp. 1333-1383.

Dawson P. et al. "Synthesis of Native Proteins by Chemical Ligation" (2000), Ann Rev Biochem 69: pp. 923-960.

Wallin, E., et al. "Genome-wide analysis of integral membrane proteins from eubacterial, archaean, and eukaryotic organisms" Protein Sci 7, (1998) pp. 1029-1038.

Sawasaki, T et al. "A bilayer cell-free protein synthesis system for high-throughput screening of gene products" FEBS Lett 514, (2002) pp. 102-105.

Frydman, J. et al. "Principles of chaperone-assisted protein folding: differences between in vitro and in vivo mechanisms" Science 272, (1996) pp. 1497-1502.

Klammt, C. et al. "High level cell-free expression and specific labeling of integral membrane proteins" Eur J Biochem 271, (2004) pp. 568-580.

Ishihara, G. et al. "Expression of G protein coupled receptors in a cell-free translational system using detergents and thioredoxin-fusion vectors" Protein Expr Purif 41, (2005) pp. 27-37.

Klammt, C et al. "Evaluation of detergents for the soluble expression of alpha-helical and beta-barrel-type integral membrane proteins by a preparative scale individual cellfree expression system" Febs J 272, (2005) pp. 6024-6038.

Bayburt, T. H. et al. "Single-molecule height measurements on microsomal cytochrome P450 in nanometer-scale phospholipid bilayer disks" Proc Natl Acad Sci U S A 99, (2002) pp. 6725-6730.

Chromy, B. A., et al. "Different Apolipoproteins Impact Nanolipoprotein Particle Formation" J Am Chem Soc. (2007) pp. 14348-14354.

Shaw, A. W., et al. "Phospholipid phase transitions in homogeneous nanometer scale bilayer discs" FEBS Lett 556, (2004) pp. 260-264.

Jonas, A et al. "Defined apolipoprotein A-I conformations in reconstituted high density lipoprotein discs" J Biol Chem 264, (1989) pp. 4818-4824.

Bayburt, T. H. et al., "Self-Assembly of Discoidal Phospholipid Bilayer Nanoparticles with Membrane Scaffold Proteins" Nano Lett. 2, (2002) pp. 853-856.

Abdulreda, M. H., and Moy, V. T. (2007) Atomic force microscope studies of the fusion of floating lipid bilayers. *Biophys J* 92, p. 4369-4378.

Adamczyk et al., The Isotope Array, a New Tool That Employs Substrate-Mediated Labeling of rRNA for Determination of Microbial Community Structure and FunctionAppl. *Environ. Microbiol.* 69, 6875-6887 (Nov. 1, 2003).

Addison, I. R. McDonald, G. Lloyd-Jones, Stable isotope probing: Technical considerations when resolving 15N-labeled RNA in gradients*J. Microbiol. Methods* 80, 70-75 (2010).

Bacher, R. Korner, A. Atrih, S.J. Foster, P. Roepstorff and G. Allmaier, Negative and positive ion matrix-assisted laser desorption/ionization time-of-flight mass spectrometry and positive ion nano-electrospray ionization quadrupole ion trap mass spectrometry of peptidoglycan fragments isolated from various bacillus species, *J. Mass Spectrom.* 36 (2001), pp. 124-139.

Baker et al. "Hydrogen Production by a Hyperthermophilic Membrane-Bound Hydrogenase in Water Soluble Nanolipoprotein Particles" (2008), *J. Amer. Chem. Soc.*, 131:7508-7509.

Bao et al., High-Sensitivity Detection of DNA Hybridization on Microarrays Using Resonance Light Scattering*Anal. Chem.*, 2002, 74:1792-1797.

Bayburt, T. H., Carlson, J. W., and Sligar, S. G. (1998) Reconstitution and imaging of a membrane protein in a nanometer-size phospholipid bilayer. *J Struct Bio*/123, p. 37-44.

Bayburt, T. H. et al., (2003) "Self-Assembly of single integral membrane proteins into soluble nanoscale phospholipid bilayers." Protein Science 12(11): 2476-2481.

Bayburt, T. H. et al., (2006) "Assembly of single bacteriorhodopsin trimmers in bilayer nanodiscs" *Archives of Biochemistry and Biophysics* 450:215-222.

Behrens et al., Linking Microbial Phylogeny to Metabolic Activity at the Single-Cell Level by Using Enhanced Element Labeling-Catalyzed Reporter Deposition Fluorescence in Situ Hybridization (EL-FISH) and NanoSIMS*Applied and environmental microbiology* 74, 3143-3150 (May 2008).

Bijsterbosch, M.K., et al., (1996) "Specific targeting of a lilophilic prodrug of iododeoxyuridine to parenchymal liver cells using lactosylated reconstituted high density lipoprotein particles." *Biochemical Pharmacology* 52:113-121.

Blanchette CD, Law R, Benner WH, Pesavento JB, Cappuccio JA, Walsworth V, Kuhn EA, Corzett M, Chromy BA, Segelke BW, Coleman MA, Bench G, Hoeprich PD, Sulchek TA. (2008) "Quantifying size distributions of nanolipoprotein particles with single-particle analysis and molecular dynamic simulations" *J Lipid Res.* 49:1420-30.

Blanchette et al., accepted (BBA membranes) *Biochim Biophys Acta.* 2009, Dec 8. [Epub ahead of print] Atomic force microscopy differentiates discrete size distributions between membrane protein containing and empty nanolipoprotein particles. 724-731.

Bockaert J., Brand C., Journot, L. (1997), Do Recombinant Receptor Assays Provide Affinity and Potency. In Receptor Classification: The integration of operational, structural, and transductional information (D.G. Trist, P.P.A. Humphrey, P. Leff, and N. P. Shankley, Eds.). vol. 812. *New York, New York Academy of Sciences*.55-70.

Boldog, T.; Grimme, S.; Li, M.; Sligar, S.; Hazelbauer, G. L. *Proceedings of the National Academy of Sciences* 2006, 103, (3 I), 11509-11514.

Borch, J.; Torta, F.; Sligar, S. G.; Roepstostf, P. Nanodiscs for Immobilization of Lipid Bilayers and Membrane Receptors: Kinetic Analysis of Cholera Toxin Binding to a Glycolipid Receptor. *Analytical Chemistry* 2008, 80, (16), 6245-6252.

Boschker et al., Direct linking of microbial populations to specific biogeochemical processes by 13C-labelling of biomarkers. *Nature* 392, 801 (1998). 801-805.

Brewer et al., Formation of Thiolate and Phosphonate Adlayers on Indium—Tin Oxide: Optical and Electronic Characterization. *Langmuir*, 18 (2002) 6857-6865.

Abstract, Brodie et al., Systems Biology Research Strategy and Technology Development: Genomic and Proteomic Strategies. Publicly disclosed on Feb. 13, 2008, http://genomicscience.energy.gov/pubs/2008abstracts/2008GTLabstracts_tech.pdf.

Brodie et al., Application of a High-Density Oligonucleotide Microarray Approach to Study Bacterial Population Dynamics during Uranium Reduction and Reoxidation. *Appl. Environ. Microbiol.* 72, 6288 (2006). 6288-6298.

Brodie et al., Urban aerosols harbor diverse and dynamic bacterial populations. *Proceedings of the National Academy of Sciences* 104, 299-304 (2007).

Brown et al., Exploring the new world of the genome with DNA microarrays *Nature Genetics*, 1999,21 :33-37.

Camarero, J. A., Kwon, Y., and Coleman, M.A. (2004) Chemoselective attachment of biologically active proteins to surfaces by

(56) References Cited

OTHER PUBLICATIONS expressed protein ligation and its application for "protein chip" fabrication. *J Am Chem Soc* 126, p. 14730-14731.

Cappuccio Cell-free Co-expression of functional membrane proteins and Apolipoprotein, forming soluble nanolipoprotein particlesl *J. Molecular and Cellular Proteomics* 7.11 (2008) pp. 2246-2253.

Casey; M. C. Seabra, (1996). "Protein Prenyltransferases". *Journal of Biological Chemistry* 271 (10): 5289-5292.

Chromy et al., (2007), Different Apolipoproteins Impact Nanolipoprotein Particle Formation. *J. Amer Chem. Soc.* 129, 14348-14354.

Civjan, N., et al., (2003) "Direct solubilization of heterologously expressed membrane proteins by incorporation into nanoscale lipid bilayers" *Biotechniques* 35:556-563.

Cline et al., Integration of biological networks and gene expression data using Cytoscape. Nat. Protocols 2, 2366 (2007).18. T. Z.

Coleman, M., Nilsson, A., Russell, T. S., Rath, P., Pandey, R., and Rothschild, K. J. (1995) Asp 46 can substitute Asp 96 as the Schiff base proton donor in bacteriorhodopsin. Biochemistry 34, p. 15599-15606.

Cornish K, Siler DJ (1996). Characterization of cis-prenyltransferase activity localized in a buoyant fraction of rubber particles from Ficus elastica latex. *Plant Physiol. Biochem.* 34:377-384.

Cornish & J.J. Blakeslee, "Rubber Biosynthesis in Plants", American Oil Chemist Society, *The Lipid Library*, Nov. 2, 2011.

Cornish, K., et al., (2012) "Natural Rubber Biosynthesis in Plants: Rubber Transferase." *Methods in Enymology* 515:63-82.

Cracknell, J. A.; Vincent, K. A.; Ludwig, M.; Lenz, 0.; Friedrich, B.; Armstrong, F. A. "Enzymatic Oxidation of H2 in Atmospheric O2: The Electrochemistry of Energy Generation from Trace H2 by Aerobic Microorganisms" *Journal of the American Chemical Society* 2008, 130,424-425.

Cullis PR and Hope MJ (1996) Physical properties and functional roles of lipids in membranes. In Biochemistry of Lipids, Lipoproteins, and Membranes (D.E. Vance and J. Vance, Eds.). vol. 20. New York: Elsevier.

Dalpke, A.H., Zimmermann, S., Albrecht, I. & Heeg, K. 2002. Phosphodiester CpG oligonucleotides as adjuvants: polyguanosine runs enhance cellular uptake and improve immunostimulative activity of phosphodiester CpG oligonucleotides in vitro and in vivo. *Immunology* 106:102-112.

DeSantis et al., High-Density Universal 16S rRNA Microarray Analysis Reveals Broader Diversity than Typical Clone Library When Sampling the Environment. *Microbial Ecology* 53, 371 (2007).

Donniger & G. Popjak, "An Improved Synthesis of Isopentenyl Pyrophosphate" (1967) *Biochem. J.* 105:545-547.

Dunn, R. J., Hackett, N. R., McCoy, J. M., Chao, B. H., Kimura, K., and Khorana, H.G. (1987) Structure-function studies on bacteriorhodopsin. I. Expression of the bacteriaopsin Gene in *Escherichia coli. J Biol Chem* 262, p. 9246-9254.

Elgren, T. E.; Zadvorny, O. A.; Brecht, E.; Douglas, T.; Zorin, N. A,; Maroney, M. J.; Peters, "Immobilization of Active Hydrogenases by Encapsulation in Polymeric Porous Gels" *Nano Letters* (2005) vol. 5, No. 10 2085-2087.

Fischer, N. O., Blanchette, C.D., Chromy, B.A., Kuhn, E.A., Segelke, B.W., Corzett, M., Bench, G., Mason, P.W. And Hoeprich, P.D. (2009). "Immobilization of His-tagged Proteins on Nickel-Chelating Nanolipoprotein Particles" Bioconjugate Chemistry 20:460-465.

Fitzgerald, K.A. And Golenbock, D.T. (2007). The Shape of Things to Come. *Science* 316:1574-1576.

Forstner, M., Peters-Libeu, C., Contreras-Forrest, E., Newhouse, Y., Knapp, M., Rupp, B., and Weisgraber, K. H. (1999) Carboxyl-terminal domain of human apolipoprotein E: expression, purification, and crystallization. *Protein Expr Purif* 17, p. 267-272.

Forte, T. M., Nichols, A. V., Gong, E. L., Levy, R. I., and Lux, S. (1971) Electron microscopic study on reassembly of plasma high density apoprotein with various lipids. *Biochim Biophys Acta* 248, p. 381-386.

Gardner et al Systems for Orthogonal Self-Assembly of Electroactive Monolayers ONAU and ITO: An Approach to Molecular Electronics. *JACS* (1995), 117:6927-6933.

Giannini, S.L., Hanona, E., Moris, P., Van Mechelen, M., Morel, S., Dessy, F., Fourneau, M.A., Colau, B., Suzich, J., Losonksy, G., Martin, M-T., Dubin G., Wettendorff, M.A. (2006). Enhanced humoral and memory B cellular immunity using HPV16/18 L1 VLP vaccine formulated with the MPL/aluminium salt combination (AS04) compared To aluminium salt only. *Vaccine* 24:5937-5949.

Goldet, G.; Wait, A. F.; Cracknell, J. A,; Vincent, K. A.; Ludwig, M.; Lenz, 0 .; Friedrich, B.; Armstrong, F. A. "Hydrogen Production under Aerobic Conditions by Membrane-Bound Hydrogenases from Ralstonia Species"*Journal of the American Chemical Society* (2008), 130, (33), 11106-1113.

Greve, Ullman's Encyclopedia of Industrial Chemistry, Rubber,2. Natural, (2012) *Wiley-VCH Verlag GmbH & Co., KGaA*, Weinheim, DOI: 10.1002/14356007.a23_225.

Gronover C.S., Daniela Wahler and Dirk Prufer (2011). "Natural Rubber Biosynthesis and Physics—Chemical Studies on Plant Derived Latex, Biotechnology of Biopolymers" *Magdy Elnashar (Ed.)*, ISBN:978-953-307-179-4.

\* cited by examiner

**Initial experimental results,  
C$^{14}$–IPP incorporation assay**

| Sample ID | 14C DPM |
|---|---|
| washed rubber particle (+) control | 926 |
| washed rubber particle w/ EDTA (-) control | 300 |
| NLP2 + WRP proteins incubated overnight | 428 |
| NLP1 + WRP proteins incubated overnight | 998 |
| NLP1 + WRP proteins incubated 1h | 2132 |
| Buffer Blank | 33 |
| 14C-IPP spike | 80022 |

Figure 4

NANOLIPOPROTEIN PARTICLES COMPRISING A NATURAL RUBBER BIOSYNTHETIC ENZYME COMPLEX AND RELATED PRODUCTS, METHODS AND SYSTEMS

CROSS REFERENCE TO RELATED APPLICATIONS

This application claims priority to US provisional application Ser. No. 61/784,288 entitled "Nanolipoprotein Particles Comprising a Rubber Synthetic Enzyme and Related Products, Methods and Systems" filed on Mar. 14, 2013 incorporated herein by reference in its entirety. This application may also be related to U.S. patent application entitled "Methods and Systems for Monitoring Production of a Target Protein in a Nanolipoprotein Particle" Ser. No. 12/118,530, filed on May 9, 2008, to U.S. patent application entitled "Methods and Systems for Producing Nanolipoprotein Particle" Ser. No. 12/118,396, filed on May 9, 2008, to U.S. application entitled "Nanolipoprotein Particles and Related Methods and Systems for Protein Capture Solubilization and/or Purification" Ser. No. 12/352,548, filed on Jan. 12, 2009, to US application "Nanolipoprotein particles and related Compositions Methods and Systems" Ser. No. 12/469,533, filed on May 20, 2009, and to US application "Nanolipoprotein particles comprising hydrogenase and related products methods and systems" Ser. No. 12/352,472, filed on Jan. 12, 2009 to the disclosure of each of which is incorporated herein by reference in its entirety.

STATEMENT OF GOVERNMENT GRANT

The United States Government has rights in this invention pursuant to Contract No. DE-AC52-07NA27344 between the U.S. Department of Energy and Lawrence Livermore National Security, LLC.

FIELD

The present disclosure relates to nanolipoprotein particles (NLPs) and in particular to NLPs comprising a rubber synthetic enzyme.

BACKGROUND

Nanolipoprotein particles (NLPs) and other particles of nanoscale dimensions have been developed to support and carry target molecules.

In particular, a number of research groups have prepared recombinant high density lipoprotein particles (rHDL) as a cell membrane mimetic for incorporating membrane proteins. The latter consists of a hydrophobic moiety or membrane interacting region that associates with the nonpolar region of the lipid bilayer and portions that are hydrophilic and extend to both the interior and exterior regions.

Constructions of catalytic systems based on nanolipoprotein particles is often challenging in view of the need to reproduce the conditions necessary to provide the enzyme in an active form.

SUMMARY

Provided herein are products, methods, and systems that are based on a cell membrane mimetic in the form of a nanolipoprotein particle that includes a natural rubber biosynthetic enzyme complex or rubber transferase complex (RuT), and allows, in several embodiments, performance in vitro or ex vivo of a polymerization reaction associated with such natural rubber biosynthetic enzymes or RuT. In some embodiments the RuT can be a collection of biological enzymes such as an enzyme capable of catalyzing rubber polymerization (cis-prenyltransferase or CPT) and/or other chemical reactions catalyzed by allene oxide synthase (AOS) and small rubber particle protein (SRPP) resulting in a rubber polymer production.

According to a first aspect, a nanolipoprotein particle is described. The nanolipoprotein particle comprises natural rubber biosynthetic enzyme complex RuT, typically comprised as a target protein, and in particular, in addition to the natural rubber biosynthetic enzyme, a membrane forming lipid, and a scaffold protein. In some embodiments the rubber biosynthetic enzymes can comprise a naturally occurring enzyme complex capable of catalyzing polymerization of natural rubber, and in particular, a naturally occurring rubber transferase enzyme complex or naturally occurring RuT.

According to a second aspect, a biocatalyst assembly is described. The biocatalyst assembly comprises a nanolipoprotein particle immobilized to a support. In the biocatalyst assembly the nanolipoprotein particle comprises RuT, typically comprised as a target protein, a membrane forming lipid, and a scaffold protein. In some embodiments of the biocatalyst assembly, the target protein can be a naturally occurring RuT.

According to a third aspect, a method to perform rubber biosynthesis is described. The method comprises providing reagents for performing biorubber synthesis and providing a nanolipoprotein particle comprising RuT, a membrane forming lipid, and a scaffold protein. The method further comprises contacting the reagents with the nanolipoprotein particle for a time and under conditions to allow rubber formation to occur. In some embodiments, the RuT is a naturally occurring enzyme complex capable of catalyzing polymerization of natural rubber.

According to a fourth aspect, a system to perform rubber biosynthesis is described. The system comprises a nanolipoprotein particle herein described, and reagents for performing said rubber biosynthesis. In the system, the nanolipoprotein particle comprises one or more RuT, a membrane forming lipid, and a scaffold protein, and the nanolipoprotein particle, and the reagents can be contacted for a time and under conditions to allow performance of the chemical reaction catalyzed by the RuT. In some embodiments, the RuT is a naturally occurring enzyme complex capable of catalyzing a polymerization reaction leading to formation of natural rubber.

According to a fifth aspect, a device for performing a rubber biosynthesis is described. The device comprises a substrate compartment, and a catalyst compartment, with the substrate compartment in communication with the catalyst compartment. In the device, the catalyst compartment comprises a biocatalyst assembly, with the biocatalyst assembly comprising a nanolipoprotein particle immobilized to a support, and with the nanolipoprotein particle comprising RuT, a membrane forming lipid, and a scaffold protein. In the device, the substrate compartment is configured to comprise a monomer for the rubber biosynthesis catalyzed by the RuT and to allow contact between said substrate and said RuT capable of catalyzing substrate polymerization. A product compartment can also be included that is in communication with the catalyst compartment and is configured to comprise a polymer produced, following the reaction of the monomers with the RuT. In some embodiments, the rubber biosynthetic enzymes are a naturally occurring enzyme complex capable of catalyzing polymerization of natural rubber, and in particular, a rubber transferase enzyme complex or RuT.

The products, methods, and systems herein described, is expected to allow in several embodiments, performance of biosynthesis of a natural rubber and more particular of a rubber polymerization in vitro or ex vivo.

The products, methods, and systems herein described can be applied in several fields including basic biology research, applied biology, bio-engineering, and additional fields, identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and the examples, serve to explain the principles and implementations of the disclosure.

FIG. 3 shows a schematic representation of a rubber production device wherein rubber is produced through a rubber polymerization reaction performed with nanolipoprotein particles comprising a RuT enzyme complex capable of performing rubber polymerization reaction.

FIG. 4 shows a table illustrating results of $C^{14}$-IPP incorporation assay of RuT comprised in an NLP.

DETAILED DESCRIPTION

Figure 1:
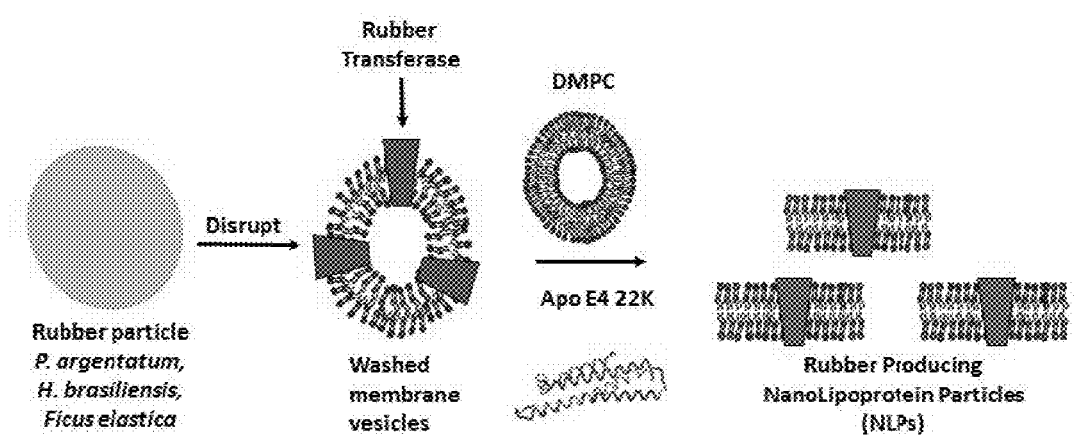
FIG. 1 shows a schematic illustration of a process, ex vivo production of Natural Rubber using NLP-stabilized biosynthetic enzymes, to provide the RuT biocatalyst-NLP according to an embodiment herein disclosed.

Nanolipoprotein particles are herein disclosed that comprise RuT in its catalytically active form and related assemblies, devices, methods and systems.

The term RuT as used herein, indicates a biocatalyst that is able to catalyze formation of natural rubber starting from organic monomers. The term "biocatalysts" as used herein, indicates biological catalysts (RuT) that are able to affect the rate of a chemical reaction, such as transformations involving organic monomeric compounds. "Rubbers" are polymers of isoprene (2-methyl-1,3-butadiene), chloroprene (2-chloro-1,3-butadiene), and/or isobutylene (methylpropene). In particular, natural rubbers comprise polymers of the organic compound isoprene typically produced with minor impurities of other organic compounds plus water. "Natural rubbers" indicate rubbers that are typically produced by living organisms such as rubber synthesizing plants. Forms of polyisoprene that are useful as natural rubbers are classified as elastomers. Synthetic rubbers are instead artificial elastomers. Currently, natural rubber is harvested mainly in the form of the latex from certain trees. The latex is a sticky, milky, colloid drawn off by making incisions into the bark and collecting the fluid in vessels.

In some embodiments, herein described, the RuT that is comprised in nanolipoprotein particles is a naturally occurring rubber transferase derived from (e.g. isolated or purified from) one or more plants. Exemplary plants are *Hevea Brasiliensis, Parthenium argentatum, Ficus elastica, Euphorbia lactifua* and additional plants identifiable by a skilled person upon reading of the present disclosure. Naturally occurring RuT is typically formed by at least three proteins comprised in a plant rubber particle (RP) and in particular, associated with the monolayer membrane of the RP. In particular, naturally occurring RuT refers typically to a complex of natural rubber biosynthetic enzymes, comprising cis-prenyl transferase (CPT), allene oxide synthase (AOS), and small rubber protein particle (SRPP) located in a monolayer membrane of the RP. In several embodiments described herein, naturally occurring RuT can be extracted from a monolayer membrane system and placed into a bilayer system for polymer synthesis. In some embodiments, in the nanolipoprotein particles and related systems described herein, the bilayer can also support rubber biosysnthesis in a plant-free manner. In several embodiments described herein a monolayer membrane protein RuT can be incorporated into a bilayer nanolipoprotein system for rubber biosynthesis.

"Rubber biosynthesis" as used herein, refers to production of natural rubber performed through at least part of the enzymatic pathway of latex-producing cells (also called laticifers) within rubber plants resulting in the formation in the cytoplasm of these plants, of rubber particles. Enzymatic pathways resulting in RP formation in laticifers have evolved during the dawn of the dicotyledoneae and are present in at least four of the dictolydonous superorders. In plants, rubber biosynthesis is catalyzed by a naturally occurring RuT membrane complex in a monolayer membrane envelope, can require two distinct substrates and a divalent cation cofactor, and typically produces a high-molecular-weight isoprenoid polymer. Purified rubber particles alone can contain all the necessary factors for the production of rubber. Rubber particles can range in size from 0.2 to 10 µm, and is dependent from species to species and within the same plant. Additionally, a correlation between rubber particle size and rubber molecular weight can be demonstrated in several species.

The term "rubber particles" as used herein indicates particles wherein biosynthesis of rubber occurs in plants. Rubber particles are surrounded by a single phospholipid membrane with hydrophobic tails pointed inward. The membrane allows biosynthetic proteins to be sequestered at the surface of the growing rubber particle, which allows new monomeric units to be added from outside the biomembrane, but within the laticifer. Typically a rubber particle is an enzymatically active entity that contains three layers of material, the rubber particle, a biomembrane, and free monomeric units (see e.g. [44]-[48] each of which incorporated herein by reference in its entirety). In RP, the biomembrane is typically held tightly to the rubber core due to the interaction involving the double bonds of the rubber polymer backbone. Free monomeric units and conjugated proteins make up the outer layer. The rubber precursor is typically isopentenyl pyrophosphate (an allylic compound), which elongates by $Mg^{2+}$-dependent condensation by the action of rubber transferase. The monomer adds to the pyrophosphate end of the growing polymer. The process displaces the terminal high-energy pyrophosphate. The reaction produces a cis polymer. The initiation step can be catalyzed by prenyltransferase, which converts three monomers of isopentenyl pyrophosphate into farnesyl pyrophosphate. The farnesyl pyrophosphate can bind to rubber transferase to elongate a new rubber polymer. In embodiments described herein, rubber biosynthesis can be performed using the RuT extracted from a lipid monolayer and placed within a bilayer NLP.

The term "nanolipoprotein particle" "nanodisc" "rHDL" or "NLP" as used herein indicates a supramolecular complex formed by a membrane forming lipid and a scaffold protein, that following assembly in presence of a target protein also include the target protein. The NLPs can function as stabilized lipid biolayer mimetics and can be comprised of biological components. In general, NLPs are discoidal in shape and have a diameter that ranges in size from 10 to 30 nm in diameter and up to 5 to 6 nm in height. The scaffold protein and target protein constitute protein components of the NLP. The scaffold proteins can be amphipathic lipoproteins in the NLP. The membrane forming lipid constitutes a lipid component of the NLP. The NLP with the incorporated proteins can also be examined by cryo electron microscopy, transmission electron microscopy, and other methods known to those skilled in the art. From electron microscopy techniques, the structures of the NLPs can be reconstructed using computational methods to obtain the three dimensional reconstructions. In several embodiments described herein, RuT has been obtained from a monolayer membrane envelope, and placed into optimized NLPs for the presentation and stabilization, of a functional enzyme complex system. Additionally, in several embodiments described herein, NLPs can be used for polymer synthesis, and in particular, can be used for rubber synthesis.

In order to obtain purified NLPs, the NLPS can be separated from impurities using Size Exclusion Chromatography (SEC), which based on the particle size, can be used to separate the NLPs from excess lipids, and excess proteins. SEC can be useful in the preliminary characterization and the purification of NLPs. Polyacrylamide Gel Electrophoreses (PAGE) can be useful for determining the purity of the sample and to give a bulk analysis of the mixed populations, for example, the mixture of complexes and the excess proteins that are unable to form a complex. In order to confirm the height, diameter and discoidal morphology of the NLPs, Atomic Force Microscopy (AFM) can be used to obtain the single particle diameter and height analysis. Additional techniques known to those skilled in the art can be used to obtain NLP purity and characterize the morphology of the NLPs.

The term "protein" as used herein indicates a polypeptide with a particular secondary and tertiary structure that can participate in, but not limited to, interactions with other biomolecules including other proteins, DNA, RNA, lipids, metabolites, hormones, chemokines, and small molecules.

The term "polypeptide" as used herein indicates an organic polymer composed of two or more amino acid monomers and/or analogs thereof. Accordingly, the term "polypeptide" includes amino acid polymers of any length including full length proteins and peptides, as well as analogs and fragments thereof. A polypeptide of three or more amino acids can be a protein oligomer or oligopeptide.

As used herein the term "amino acid", "amino acidic monomer", or "amino acid residue" refers to any of the twenty naturally occurring amino acids including synthetic amino acids with unnatural side chains and including both D and L optical isomers. The term "amino acid analog" refers to an amino acid in which one or more individual atoms have been replaced, either with a different atom, isotope, or with a different functional group but is otherwise identical to its natural amino acid analog.

The term "scaffold protein" as used herein indicates any protein that is capable of self-assembly with an amphipathic lipid in an aqueous environment, organizing the amphipatic lipid into a bilayer, and include but are not limited to apolipoproteins, lipophorines, derivatives thereof (such as truncated and tandemly arrayed sequences) and fragments thereof (e.g. peptides), such as apolipoprotein E4, 22K fragment, liphorin III, apolipoprotein A-1, apolipophorin III from the silk moth B. mori, and the like. In particular, in some embodiments rationally designed amphipathic peptides can serve as a protein component of the NLP.

In some embodiment, the peptides are amphipatic helical peptides that mimic the alpha helices of an apolipoprotein component that are oriented with the long axis perpendicular to the fatty acyl chains of the amphipatic lipid and in particular of the phosphoplipid.

The term "target protein" as used herein indicates any protein having a structure that is suitable for attachment to or association with a biological membrane or biomembrane (i.e. an enclosing or separating amphipathic layer that acts as a barrier within or around a cell). In particular, target proteins include proteins that contain large regions or structural domains that are hydrophobic (the regions that are embedded in or bound to the membrane); those proteins can be extremely difficult to work with in aqueous systems, since when removed from their normal lipid bilayer environment those proteins tend to aggregate and become insoluble. Accordingly, target proteins are protein that typically can assume an active form wherein the target protein exhibits one or more functions or activities, and an inactive form wherein the target protein doe not exhibit those functions/activities. Exemplary target proteins include but are not limited to membrane proteins, i.e. proteins that can be attached to, or associated with the membrane of a cell or an organelle, such as integral membrane proteins (i.e. proteins (or assembly of proteins) that are permanently attached to the biological membrane.), or peripheral membrane proteins (i.e. proteins that adhere only temporarily to the biological membrane with which they are associated). Integral membrane proteins can be separated from the biological membranes only using detergents, nonpolar solvents, or sometimes denaturing agents. Peripheral membrane proteins are proteins that attach to integral membrane proteins, or penetrate the peripheral regions of the lipid bilayer with an attachment that is reversible.

"Detergents" as described herein, refer to amphipathic molecules, or molecules that can contain both a nonpolar "tail" having aliphatic or aromatic character and a polar "head". Ionic character of the polar head group forms the basis for broad classification of detergents in ionic (charged, either anionic or cationic), nonionic (uncharged) or zwitterionic (having both positively and negatively charged groups but with a net charge of zero) detergents. In biological research, detergents can be used to lyse cells (release soluble proteins), solubilize membrane proteins and lipids, control protein crystallization, prevent nonspecific binding in affinity purification and immunoassay procedures, and as additives in electrophoresis. Exemplary detergents that can be used in methods and procedures herein described comprise ionic detergents such as amphipol A8-35, cholic acid, deoxycholic acid, LysoFos glycerol, sodium dodecanoyl sarcosine, cetyl methyl ammonium bromide, and sodium dodecyl sulfate; nonionic detergents such as Triton X-100, Brij 35, Tween 20, Tween 80, and octyl β-glucoside; bile acid salts; and/or zwitterionic detergents such as CHAPS, CHAPSO and Sulfobetaine; as well as additional detergents identifiable by a skilled person upon reading of the present disclosure.

In some embodiments, detergent monomers can be used to solubilize membrane proteins by partitioning into the membrane bilayer or a membrane monolayer. With increasing amounts of detergents, membranes can then undergo various stages of solubilization. The initial stage is lysis or rupture of the membrane. A detergent:membrane lipid molar ratio of 0.1:1 through 1:1 the lipid bilayer usually remains intact but selective extraction of some membrane proteins occurs. Increasing the ratio to 2:1, solubilization of the membrane occurs resulting in mixed micelles. These include phospholipid-detergent micelles, detergent-protein micelles, and lipid-detergent-protein micelles. At a ratio of 10:1, all native membrane lipid:protein interactions are effectively exchanged for detergent:protein interactions.

The amount of detergent that can be used for protein extraction depends on the CMC, aggregation number, temperature and nature of the membrane and the specific detergent as will be understood by a skilled person. The solubilization buffer typically contains sufficient detergent to provide greater than 1 micelle per membrane protein molecule to ensure that individual protein molecules are isolated in separate micelles. In several embodiments described herein, detergents are used in a buffer to solubilize the RuT from the lipid monolayer prior to incorporation of the RuT into NLPs. The detergent can be removed by dialysis using techniques identifiable by those skilled in the art. In an exemplary embodiment, the detergent used for solubilizing can be for example cholate (e.g. about 20 mM) in standard phosphate buffered saline (PBS) or tris buffered saline (TBS) at pH about 7.5 which can then be removed by dialysis according to techniques and procedures identifiable by a skilled person.

In embodiments of the nanolipoprotein particles herein disclosed, at least one target protein of the NLP is a rubber synthetic enzyme and in particular a rubber transferase complex or RuT.

The term "rubber transferase" (RuT) identifies enzymes that can catalyze the chemical reaction:

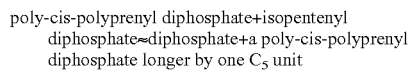

Thus, the two substrates of this enzyme are typically poly-cis-polyprenyl diphosphate and isopentenyl diphosphate, whereas its two products are diphosphate and poly-cis polyprenyl diphosphate longer by one C5 unit. It should be noted that naturally occurring rubber particles contain in addition to cis-prenyl transferase (CPT) to additional enzymes—allene oxise synthase (AOS) and small rubber protein particle (SRPP)—the two proteins are required for biosynthesis of natural rubber.

Exemplary rubber synthetic enzymes comprise a rubber transferase complex from guayule (*P. argentatum*), para rubber tree (*H. brasiliensis*) and Russian dandelion (*T. koksaghyz*), and additional rubber transferase identifiable by a skilled person. The enzymes can be used as cloned enzymes and can also be derived from crude RP membranes.

In some embodiments the RuT is capable of catalyzing rubber polymerization and in particular production of natural rubber. Natural Rubber (NR) is a raw material used throughout the world with an annual global consumption rate topping 10 million metric tons; overall world-wide demand is projected to increase markedly over the next decade (1,2). Typically NR comprises a renewable, high molecular weight cis-polyisoprene exhibiting durable elasticity and other performance/material properties identifiable by a skilled person in comparison with petroleum-derived "synthetic" rubber or SR. Typically, natural rubber can be harvested from *Hevea* rubber trees and processed into crude rubber that can be further elaborated into a variety of products. The bulk of NR is typically used to produce tires and is often blended with synthetic rubber (SR), the latter being comprised of butadiene, isoprene, styrene, and isobutylene.

Rubber biosynthetic enzymes capable of catalyze formation of NR typically reside in rubber particles (RP) contained within the plant interstices; most, if not all of the biosynthetic enzymes are associated with a cellular membrane structure embodied in the RPs. Typically, in nature, rubber particles are formed in the cytoplasm of specialized latex producing cells called laticifers within rubber synthesizing plants [38]. Rubber particles are surrounded by a single phospholipid membrane with hydrophobic tails pointed inward. The membrane allows biosynthetic proteins to be sequestered at the surface of the growing rubber particle, which allows new monomeric units to be added from outside the biomembrane but within the lacticifer. The rubber particle can be considered an enzymatically active entity that contains three layers of material, the rubber particle, a biomembrane, and free monomeric units. The biomembrane is held tightly to the rubber core due to the interactions of the membrane with the double bonds of the rubber polymer backbone [39]. In RPs, free monomeric units and conjugated proteins make up the outer layer. The rubber precursor is isopentenyl pyrophosphate (an allylic compound), which elongates by $Mg^{2+}$-dependent condensation by the action of rubber transferase. The monomer adds to the pyrophosphate end of the growing polymer [40]. The process displaces the terminal high energy pyrophosphate. The reaction produces a cis polymer. The initiation step is catalyzed by prenyltransferase, which converts three monomers of isopentenyl pyrophosphate into farnesyl pyrophosphate [41]. The farnesyl pyrophosphate can bind to rubber transferase to elongate a new rubber polymer. The required isopentenyl pyrophosphate is typically obtained from the mevalonate (MVA) pathway, which is derives from acetyl-CoA in the cytosol. In plants, isoprene pyrophosphate can also be obtained from 1-deox-D-xyulose-5-phosphate/2-C-methyl-D-erythritol-4-phosphate pathway within plasmids [42]. The relative ratio of the farnesyl pyrophosphate initiator unit and isoprenyl pyrophosphate elongation monomer determines the rate of new particle synthesis versus elongation of existing particles.

In embodiments herein described functional rubber biosynthetic enzymes, can be cloned and expressed fabricate NLP structures that contain functional NR biosynthetic enzymes and possibly build a device to enable "ex vivo" rubber biosynthesis. In some embodiments, biosynthetic enzymes can be obtained from the genomes of guayule (*P. argentatum*), para rubber trees (*H. barsiliensis*) and Russian dandelions (*T. koksaghyz*) as well as other rubber latex producing plants and express them in NLP constructs. Exemplary rubber producing enzymes comprise cis-prenyl transferase (CPT), allene oxide synthase (AOS) and small rubber particle protein (SRPP). In some embodiments NLP constructs containing the biosynthetic enzymes will be housed in a device that enables application of industrial biotechnology production/manufacturing tenets. In some embodiments, NLPs comprising rubber producing enzymes is expected to allow a scalable processes and lower overall raw material and production costs.

In embodiments of the nanolipoprotein particles herein disclosed the rubber synthetic enzyme, e.g. the enzyme capable of catalyzing rubber polymerization or other rubber synthesis, is comprised in a functional or active form, i.e. performing or able to perform, under appropriate conditions, one or more of the functions associated to the rubber polymerization in a system, such as an organism, from which the biocatalyst has been derived.

In embodiments herein described, the RuT is comprised in the NLP together with membrane forming lipids. The term "membrane forming lipid" or "amphipathic lipid" as used herein indicates a lipid possessing both hydrophilic and hydrophobic properties that in an aqueous environment assemble in a lipid bilayer structure that consists of two opposing layers of amphipathic molecules known as polar lipids. Each polar lipid has a hydrophilic moiety, i.e., a polar group such as, a derivatized phosphate or a saccharide group, and a hydrophobic moiety, i.e., a long hydrocarbon chain. Exemplary polar lipids include phospholipids, sphingolipids, glycolipids, ether lipids, sterols and alkylphosphocholines. Amphipathic lipids include but are not limited to membrane lipids, i.e. amphipathic lipids that are constituents of a biological membrane, such as phospholipids like dimyristoylphosphatidylcholine (DMPC) or dioleoylphosphoethanolamine (DOPE) or dioleoylphosphatidylcholine (DOPC), or dipalmitoylphosphatidylcholine (DPPC). Additional exemplary polar lipids include synthetic phospholipid-based asymmetric bola-amphiphile mimetic of the natural lipids in archaea. (Sun, X. et al 2006), which are particularly suitable in embodiments, wherein performance of reactions at a high temperature is desired since the structure of the archaea lipids is thought to keep the membrane intact at upwards of 90° C. (see also [23]). In some embodiments, the temperatures can be maintained below about 30° C. In some of those embodiments the average temperature can be about 23.8° C. In some embodiments the range of temperatures for the reaction can be from about 22° C. to about 25° C. In embodiments in which DMPC is used, the temperature can be about 28.7° C.

The membrane forming lipid and the protein components of the NLP are generally able to self-assemble in a biological (largely aqueous) environment according to the thermodynamics associated with water exclusion (increasing entropy) during self-assembly.

In some embodiments of the methods and systems herein provided, the amphipathic lipid and the protein components of the NLP are allowed to assembly in a cell free expression system.

"Cell free" as described herein, indicates an in vitro tool widely used to study biological reactions that happen within cells while reducing the complex interactions found in a whole cell. Additionally, cell free can also be used to perform enzymatic activity utilizing a cell's organelles to perform the enzymatic reaction of interest. In order to obtain the organelles of interest, subcellular fractions can be isolated by ultracentrifugation to provide molecular machinery that can be used in reactions in the absence of many of the other cellular components.

Cell-free biosystems indicate extracts made from whole cell preparations. The systems can be prepared by mixing a number of purified enzymes and coenzymes. Cell-free biosystems can be used as a low-cost biomanufacturing platform compared to microbial fermentation used in standard laboratory procedure. Cell-free in vitro biosystems can be controlled and accessed without membranes or with membranes, and/or detergents and lipids. For example, cell-free protein synthesis is becoming a new alternative choice for fast protein synthesis. In cell-free biosystem, high product yields can be accomplished without the formation of by-products or the synthesis of cell mass. In vitro biosystems can implement some biological reactions that living microbes or chemical catalysts cannot implement before. Enzymatic systems without the barrier of cellular membrane usually have faster reaction rates than microbial systems. Enzyme cocktails can be enabled to tolerate toxic compounds as will be understood by a skilled person. Enzyme mixtures usually work under broad reaction conditions, such as high temperature, low pH, the presence of organic solvents or ionic liquids. Exemplary methods of obtaining proteins via cell free systems can be found in Cappucchio et al [49] and in additional references identifiable by a skilled person upon reading of the present disclosure (see also Example 9).

In particular, the NLP components can be contacted to form an admixture that then can be subjected to a temperature transition cycle in presence of a detergent. In the temperature cycle, the temperature of the admixture is raised above and below the gel crystalline transition temperature of the membrane forming lipids. Exemplary procedures expected to result in formation of an NLP comprising a biocatalyst comprise in situ incorporation of the biocatalyst into self-assembling NLPs (according to procedure where lipid, scaffold, biocatalyst, possibly surfactant are added together and subjected to transition temp fluctuation to assemble NLPs and incorporate biocatalyst simultaneously) A further description of this method can also be found in the U.S. patent application entitled "Nanolipoprotein Particles and Related Methods and Systems for Protein Capture Solubilization and/or Purification" Ser. No. 12/352,548 filed on Jan. 12, 2009 and incorporated herein by reference in its entirety. Additionally the RuT-NLPs herein disclosed are also expected to be provided by incubation of preformed NLPs with the RuT and possibly surfactant, and the "one pot" synthesis, where gene sequences encoding the biocatalyst and scaffold protein are used to direct the (cell-free) synthesis of the necessary NLP components in "one pot" extensively described in U.S. patent application entitled "Methods and Systems for Producing Nanolipoprotein Particle" Ser. No. 12/118,396 filed on May 9, 2008 herein incorporated by reference in its entirety. The RuT can be supplied in the following forms in the above variants: inside the native membrane, purified from the native membrane, in natural or artificial liposomes. The RuT can also be expressed recombinantly in another organism such as *E. coli*, and be used in the recombinant form in the native membrane, liposomes, or purified.

Assembly of RuT can be detected using techniques identifiable by the skilled person upon reading of the present disclosure that include Atomic Force Microscopy or Transmission Electron Microscopy. The insertion of biocatalyst in NLPs can be inferred from a comparison of size between empty NLP and supposed biocatalyst NLP using: Size Exclusion Chromatography, Native, and denaturing Poly-Acrylamide Gel Electrophoresis, and a height comparison in AFM. Additionally, in using gel electrophorese to examine the complex and proteins within the complex, protein spots can also be excised out of the gel and mass spectrometry can be used to identify the proteins through trypsin fragmentations. In embodiments described herein, the RuT complex with NLP obtained can be of a size of 20+/−5 nm, obtained by SEC.

The term "detect" or "detection" as used herein indicates the determination of the existence, presence or fact of RuT-NLP and/or related activities in a limited portion of space, including but not limited to a sample, a reaction mixture, a molecular complex and a substrate. A detection is "quantitative" when it refers, relates to, or involves the measurement of quantity or amount of the biocatalyst, biocatalyst-NLP and/or related activities (also referred as quantitation), which includes but is not limited to any analysis designed to determine the amounts or proportions of the biocatalyst, biocatalyst NLP and/or related activities. A detection is "qualitative" when it refers, relates to, or involves identification of a quality or kind of the biocatalyst, biocatalyst-NLP and/or related activities in terms of relative abundance to another biocatalyst, biocatalyst-NLP and/or related activities, which is not quantified.

The assembled RuT-NLPs include the rubber synthetic enzyme complex or RuT in a functional or active form and in particular the biocatalytic active site can catalyze rubber formation by polymerization pf isoprenyl pyrophosphate (IPP). In several embodiments described herein, detecting the enzyme activity in the NPL can be performed using an assay based on $^{14}C$ IPP incorporation (see e.g. Example 8) as well as by additional techniques identifiable by a skilled person.

In several embodiments, a RuT-NLP can contain a mass ratio of between 1:1 and 20:1 of lipid to scaffold protein. The ratio of scaffold protein to RuT can be varied from 1:0.025 to 1:1. The concentration of membrane forming lipid can be varied from 0.1 to 20 mg/per mL. A skilled person will be able to identify the appropriate ratios based on the size and dimension (lipid to scaffold protein ratio) and the protein-protein interactions (Scaffold protein to rubber synthetic enzyme ratio) characterizing the rubber synthetic enzyme complex or RuT of choice.

Enzyme stability can be varied due to the rubber transferase species, accession, degree of purification, assay conditions and assay temperatures. In order to check stability one can determine the linear range of incorporation rate with time in order to generate kinetic comparisons. For example, RPs from *P. argentatum* strain 593 would generate a low limit of detection at 25° C. at 1 hour of an activity assay in comparison to another transferase from another species such as *P. argentatum* strain 11491 which is more stable at this temperature for a much longer time [43]. A person skilled in the art can determine the optimal temperatures depending on the species used, and in the conditions in which the RuT are incorporated into NLPs.

In order to test the stability and the activity of the RuT within NLPs, rubber transferase activity can be measured by IPP incorporation rates as well as performing a kinetic analysis of the RuT within the NLPs to analyze the rubber biosynthesis. In a kinetic analysis, the synthesis of rubber depends on the concentrations of FPP (initiator), IPP (monomeric) and magnesium ions (the activators). Kinetic constants can be determined for each by varying the concentrations one at a time, while the other two are present in nonlimiting but noninhibitory concentrations. These constants can also vary over several orders of magnitude in different rubber producing species for the initiator and over at least one order of magnitude for the magnesium ion activator. Thus, several species-specific experiments can be required to find the appropriate concentration ranges for good kinetic data and can the amount of experimentation can be determined by one skilled in the art. Depending on which aspect of rubber biosynthesis is under investigation, the initiation reaction, the polymerization reaction, or both simultaneously (as is most common), different kinetic analyses are appropriate. (43) In general, a Michaelis-Menton plot of 1/v versus 1/[APP] can generally result in a curved plot, leading to a subjective linear regression and a doubtful $Km_s$. For the IPP polymerization reaction, in the presence of nonlimiting initiator concentrations, the Eadie-Hofstee plot of v/[S] versus [S] can generate a linear plot over most concentrations but very low IPP concentrations and nonlimiting IPP concentrations should be deleted. The gradient of the plot is $-Km^{IPP}$, and the y-axis intercept is $V_{max}^{IPP}$ for IPP in the particular initiator used. However, short initiators can also generate curved v/[S] versus [S] plots. In these circumstances, using a Hill plot can be used to obtain a Hill plot of $\log(v-V_{max})/v$ plotted against log [S]. In this plot, the $Km^{APP}$ is the x-axis value where y=1.

Functionality of the RuT comprised in the NLP can also be detected by several techniques that are based on the detection of the polymer that is produced. Exemplary techniques to detect the biocatalyst activity include detection of polymer production catalyzed by a RuT-NLP. Additional techniques to detect rubber synthetic enzyme activity are identifiable by a skilled person upon reading of the present disclosure.

In several embodiments, where the rubber synthetic enzyme is from a living organism, the biocatalyst activity detected for RuT-NLPs is expected to be comparable with the activity of the native rubber biosynthetic enzyme complex in the biological environment where RuT is derived.

In several embodiments, RuT-NPL herein described can be used in method to perform a rubber synthesis, and in particular, in embodiments where the RuT is derived from an organism, to perform in vitro a rubber polymerization that can be performed and in particular is catalyzed by the rubber synthetic enzyme in the organism in vivo.

The wording "polymerization" relates to a process of reacting monomer molecules together in a chemical reaction to form polymer chains or three-dimensional networks. In particular, synthesis of a rubber is performed by polymerization of an organic monomer such as nucleotide, amino acid, isoprene and additional monomers identifiable by a skilled person. In several embodiments described herein, polymerization synthesis, and in particular rubber polymerization, is performed using NLPs.

The terms "catalyzed", "catalyze" and "catalysis" as used herein relates to the process in which the rate of a chemical reaction is increased by means of a chemical substance known as a catalyst, which in the present application, is a biosynthetic enzyme and in particular a membrane bound biosynthetic enzyme.

The wording "in vitro", as used herein, indicates a technique of performing a given procedure in a controlled environment outside of a living organism and includes any procedures experimentations or measurements done in an artificial environment outside the living organism comprising the procedures commonly identified as "ex vivo". The term "organism" and in particular "living organism" as used herein indicates an individual biological system capable to carry on the activities associated with life, which includes but is not limited to animal, plant, fungus, or micro-organisms. In at least some form, organisms are capable of reacting to stimuli, reproduction, growth and maintenance as a stable whole. An organism can be unicellular or multicellular, which include organisms, such humans, constituted by many billions of cells grouped into specialized tissues and organs. Exemplary living organisms for the rubber synthetic enzyme-NLPs of the present disclosure include but are not limited to several plant organism *Guayule*, *Ficus*, *Hevea*, and *Taraxacum koksaghyz*.

In some embodiments, the chemical reaction catalyzed by RuT-NLP is polymer production and in particular rubber production, and the NLPs incorporated with RuT can be used to catalyze production of the polymer starting from an organic substrate that is processed to provide polymers produced by RuT-NLPs.

In certain embodiments wherein the reaction is performed as a solution phase reactions, RuT-NLPs can be used at high concentrations and also can provide access to substrate of biosynthesis. In some embodiments, a RuT in NLPs reaction can be performed with a rubber biosynthetic enzyme in a soluble and functional form without need of surfactants. In some embodiments, the nanoscale dimensions of the NLPs enable a high packing density of RuT. Additionally, RuT-NLPs can be attached to a solid phase support (through the apolipoprotein) in such a way as to provide access to both sides of the lipid bilayer, providing increased access of the reactants to the active site of the biocatalyst. In several embodiments, during use of purified membrane proteins, the proteins are stabilized in the conditions in which the proteins are dissolved (e.g. about 20 mM cholate in PBS or TBS).

A skilled person will be able to identify the above procedures and any appropriate or necessary variations upon reading of the present disclosure and in particular of the detailed description and the examples section.

In several embodiments of the present disclosure, reagents for the performance and/or detection of a chemical reaction catalyzed by RuT-NLPs herein disclosed, and can be provided in systems for performing the chemical reaction, also including the appropriate rubber biosynthetic enzymes.

In particular, in some embodiments RuT can be supplied in the following forms in the above variants: inside the native membrane, purified from the native membrane, in natural or artificial liposomes. In some embodiments RuT can also be expressed recombinantly in another organism such as *E. coli*, and be used in the recombinant form in the native membrane, liposomes, or purified. In some embodiments, purification of RuT-NLP can be performed to obtain a purification of the RuT greater than about 90% (see e.g. Example 10).

In the kit of parts herein disclosed, the components of the kit can be provided, with suitable instructions and other necessary reagents, in order to perform the methods here disclosed. In some embodiments, the kit can contain the compositions in separate containers. Instructions, for example written or audio instructions, on paper or electronic support such as tapes or CD-ROMs, for carrying out the assay, can also be included in the kit. The kit can also contain, depending on the particular method used, other packaged reagents and materials (i.e. wash buffers and the like).

In some embodiments, RuT-NLPs provide a well-defined water-soluble matrix that maintains the enzymatic activity and that is amenable to incorporation into more complex architectures.

Exemplary architectures comprise RuT suitable for polymerizing rubber, wherein RuT-NLPs herein described is immobilized to a suitable support or scaffold.

The term "support" as used herein indicates any material or substance suitable to hold up or serve as a foundation or prop for the biocatalyst-NLPs herein described.

In some embodiments, a support for RuT-NLP comprises a material for attaching RuT-NLPs to immobilize RuT-NLPs to a solid phase so that RuT-NLPs can be isolated from the liquid phase which can then be removed and replenished.

The term "immobilize" as used herein indicates the act or the condition of reducing up to minimizing or eliminating the motion of a biocatalyst-NLP. In particular, in some embodiments, RuT-NLP can be immobilized via a chemical linkage to the NLP lipid or a chemical linkage through the apolipoprotein. The chemical linkage through the lipid can be provided, for example, using a biotin labeled lipid and attaching the protein avidin to the surface of the support. Additionally, the NLP can be attached through the apolipoprotein using a histidine tag on the protein and attaching to a Nickel-NTA terminated support. The latter is described in detail in [15]. The NLP can also be attached through other chemical linkages from the apolipoprotein, for example, through lysine residues an amide bond can be formed between the apolipoprotein and a support functionalized with carboxylic acid groups. In some embodiments cross-linking the carboxylic acid groups can be performed by contacting cinnamate esters with the NLP to cross link the NLP onto a support, according to approaches identifiable to those skilled in the art.

In some embodiments, the RuT-NLPs can also be immobilized to solid supports for heterogeneous catalysis, which would provide the opportunity to flush reaction byproducts which could poison the catalyst activity, and/or provide the opportunity to regenerate the catalyst using reducing agents that can then be easily removed. In particular in some embodiments, RuT-NLP can be immobilized to a support configured to enable, and in particular optimize production of rubber.

In some embodiments, RuT-NLPs herein disclosed and/or related assemblies, allows improvements of an ex vivo enzymatic strategy, in particular when stable, active biocatalyst can be immobilized on surfaces for reactant cycling and to prevent catalyst poisoning from reaction byproducts. In some embodiments, reactions can be performed can be performed using sterilized reagents, distilled pyrogen free water, or commercial sterilized water for injection, in order to minimize occurrence catalyst poisoning.

In some embodiments, RuT-NLPs herein described are expected to find application in a linked network of chemical processes that produces rubber or other polymers.

In some embodiments, NLPs comprising rubber producing polymer is expected to be useful to provide a source of natural rubber (NR) through an efficient source for producing a raw material (natural rubber or NR) using nanoparticle technology.

Additional uses and embodiments of RuT-NLPs herein disclosed are based on the ability of RuT-NLP to allow attachment of a functional membrane-bound rubber biosynthetic enzyme to a solid support using the surrounding NLP as an attachment point and additional parameters identifiable by a skilled person.

Exemplary architectures include devices, such as biomimetic hydrogen production devices, for performing one or more reactions catalyzed by -RuT-NLP of interest. An example of such a device is illustrated in Example 7 wherein a hybrid microbial fuel cell is schematically illustrated. Additional devices can include a "hybrid self-contained biohydrogen production and storage device".

Further details concerning the nanoparticles, assemblies, devices, methods and systems herein disclosed, can be identified by the person skilled in the art upon reading of the present disclosure.

EXAMPLES

The methods and system herein disclosed are further illustrated in the following examples, which are provided by way of illustration and are not intended to be limiting.

In particular, in the following examples, a further description of the nanoparticles methods and systems of the present disclosure is provided with reference to exemplary applications. A person skilled in the art will appreciate the applicability of the features described in detail for nanoparticles comprising enzyme capable of catalyzing rubber polymerization from to nanoparticles including other rubber synthetic enzymes as defined herein.

Example 1

Preparation of RuT-NLPs

Nanolipoprotein particles comprising a rubber synthetic enzyme can be formed according to the approach schematically illustrated in FIG. 1.

In particular, FIG. 1 provides an overview of the process used to assemble RuT-NLPs: Plant cells were first lysed and cellular membranes were separated and washed using centrifugation, forming insoluble membrane fragments and vesicles.

In particular in the illustration of FIG. 1 fabrication of NLPs such that during particle formation, rubber particle membrane preparations are added to self-assembling mixture of apolipoproteins, phospholipids and co-factors. When NLP self-assembly reaction is complete, stable inclusion of rubber transferase enzyme(s) from rubber particle membranes will be achieved, i.e. active rubber biosynthetic enzymes (rubber transferase enzymes) will be incorporated into NLP constructs, with full retention of activity; this process is outlined in the FIG. 1.

In essence, during the self-assembly of the NLP, the rubber biosynthetic enzymes or rubber transferase enzymes contained in the crude membranes prepared from rubber particles will be incorporated into NLP constructs with full retention of biological activity. An alternative representation of this approach is shown in FIGS. 2 and 3.

Figure 2:
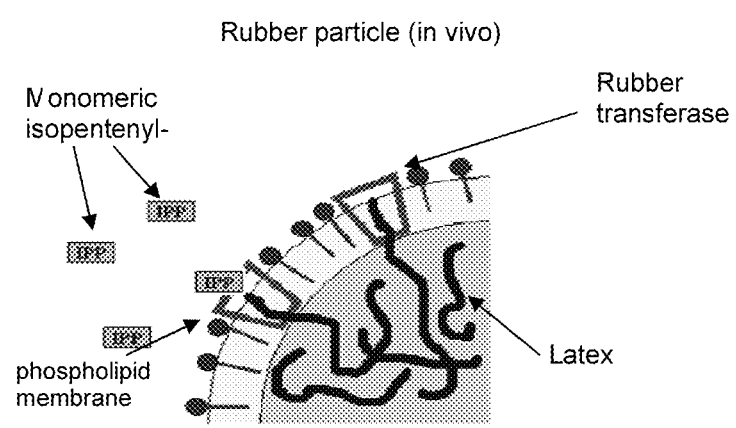
FIG. 2 shows a schematic representation of a rubber particle structure.
Figure 3:
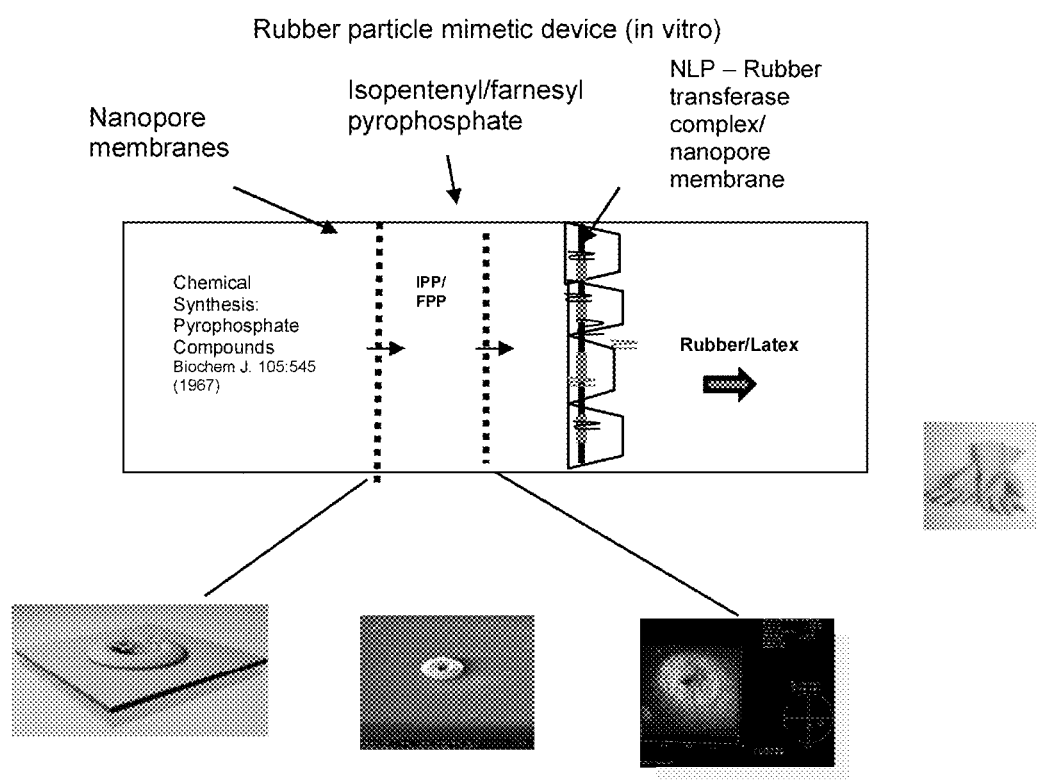
FIG. 3 shows a schematic representation of a biocatalyst device according to an embodiment herein disclosed. In particular.

In the approaches illustrated in FIGS. 1 to 3, biosynthetic enzymes that comprise the rubber transferase complex are contained within NLPs structures in a manner similar to that described previously for bacterial enzymes. These particles are compartmentalized such that monomeric substrates farnesyl pyrophosphate (polymer initiation) and isopentenyl pyrophosphate (IPP) can added/presented to the rubber transferase-NLP complex and biosynthesis of natural rubber ensues. IPP can be affordably prepared on scale from known and established synthetic routes.

Example 2

Identification and Characterization of Rubber Synthetic Enzyme/NLPs: Size Exclusion Chromatography Rubber synthetic enzyme/NLPs produced are expected to be produced according to a procedure exemplified in Example 1. The particles are expected to be separated from unincorporated free proteins and lipids using size exclusion chromatography (SEC). Size exclusion chromatography can be performed using a Superdex 200 (GE Healthcare Life Sciences) calibrated with a standard commercial molecular weight kit, where the chromatography analysis is performed with an Akta system. Standard size exclusion chromatography can be used to obtain purified RuT NLPs, obtained on a superdex 200 PC, using a PBS buffer at pH 7.5 and a flow of elution at 0.15 mls/minute for purification.

Native and denaturing polyacrylamide gel electrophoresis of the SEC fractions are expected to be carried out according to published procedures. [16, 17]

Example 3

Characterization of Rubber Synthetic Enzyme/NLPs: Atomic Force Microscopy

Nanolipoprotein particles are expected to be produced and separated from unincorporated free proteins and lipids using size exclusion chromatography (SEC) as exemplified in Example 2. The resulting fractions are expected to be characterized for size and homogeneity by native and denaturing gel electrophoresis and atomic force microscopy (AFM).

In particular, gel electrophoresis of the SEC fractions from assembly A are expected to support the formation of NLPs containing proteins from the cell solubilized membranes. In order to determine the morphology and size distribution of these particles, the SEC fractions are expected to be characterized with AFM. Atomic force microscopy (AFM) is expected to be carried out according to published procedures. [16, 17] Three dimensional reconstructions of the complexes can be carried out using electron microscopy followed by computational structural analysis, or structural image analysis.

Example 4

Ex Vivo Production of NLPs Comprising Rubber Polymerization Catalyst

Applicants expect to develop an ex vivo rubber production capability that does not rely on any rubber producing plant per se but rather on an approach utilizing our NLP nanoparticle technology. In essence, NLPs containing functional rubber biosynthetic enzyme(s)—rubber transferase (RT)—will be fabricated in a manner analogous to the approach Applicants developed for hydrogen production using NLP-hydrogenase constructs [31]. It is anticipated that NLP-RT will produce cis-1,4 polyisoprene from monomeric substrate, isopentenyl pyrophosphate (IPP); the latter will be synthesized in bulk using established methodology [32].

The process of rubber biosynthesis will be monitored using an established assay that measure incorporation of radiolabeled isopreneyl-pyrophosphate or IPP. This assay provides a quantitative perspective on the overall biologically catalyzed polymerization reaction [43].

Ex vivo rubber synthesis has been demonstrated using rubber particles purified from guayule, Ficus, Hevea, and Taraxacum koksaghyz—a rubber producing dandelion [35]. In the latter case, intact RP were prepared and rubber transferase (RT) activity measured and quantified using $^{14}$C-labelled isopentenyl pyrophosphate (IPP); the label was uniformly incorporated into polyisoprene chains within the rubber particle. Fabrication of high molecular weight polyisoprene rubber by an ex vivo process is expected to be performed in accordance with the disclosure with nanolipoprotein particles (NLP) and guayule rubber transferase (RT) obtained from crude, disrupted RP membranes;

A suitable method expected to be applicable to the formation of RuT-NLP of the disclosure is the method described in US application "Nanolipoprotein particles comprising hydrogenase and related products methods and systems" Ser. No. 12/352,472, filed on Jan. 12, 2009.

In particular, a process to produce natural rubber in NLP is expected to include: 1) reconstitution of functional membrane-associated rubber transferase (RuT) from rubber particle membrane preparations into stable NLP constructs; and 2) utilize molecularly expressed rubber transferase (RuT) enzymes (CPT, AOS, SRPP, etc.). Applicant will fabricate NLPs containing biosynthetic enzyme(s); NLPs are the product of self-assembly between apolipoproteins and phospholipids yielding uniform nanoparticles (10-25 nm). If a solubilized membrane associated protein, e.g. RuT, is included during NLP formation, it will be incorporated within the NLP during self-assembly, often with complete retention of biological activity [31, 33]. Alternatively, in situ NLP-RuT construct formation might be possible using cell-free systems containing lipids and apolipoproteins as we have described previously [34], [49].

In either case, it is anticipated the rubber biosynthetic enzymes will function and polymerize isoprene-pyrophosphate (IPP) monomers into high molecular weight rubber. Polymer synthesis will be initiated allylic pyrophosphate primer molecule, farnesyl pyrophosphate, followed by addition of IPP monomer; the latter will be prepared by total chemical synthesis from isopropyl alcohol [32]. Rubber polymer formation will be monitored using an established assay system that measures incorporation of radiolabeled (e.g. carbon-14) IPP monomer. Using an appropriately designed reaction vessel that separates reactants from product, isopentyl pyrophosphate (IPP) will be added and high molecular weight polyisoprene polymer will be produced, extracted and characterized by scientists at the USDA-ARS laboratory.

Target genes for rubber synthesis will include as part of RuT: cis-1,4-isopentyl pyrophosphate transferase (CPT), as well as, or in concert with: allene oxide synthetase or AOS (Cyp 450 74A2) and small rubber protein particle or SRPP [28].

At least in some embodiments high quality natural rubber is expected to be produced in a system based on isolated rubber biosynthetic enzymes stabilized in a nanoparticle environment. In particular, in some embodiments the strength of this approach is expected to comprise: 1) creation of a flexible system that will enable cost-effective NR production and provide a molecular means to begin to understand more fully processes associated with NR biosynthesis and/or 2) eliminating the cost associated with NR production through manual extraction of NR.

Example 5

Production, Identification and Uses of Rubber Polymerization Catalysts

Production of a rubber polymerization catalyst (RuT)/NLPs is expected to be performed as follows. Briefly, cellular membranes from rubber particles such as the on illustrated in FIG. 2 can be separated from cellular debris and washed using centrifugation (see FIG. 1 and Example 1). A suspension of the membranes can be added to a mixture of phospholipid 1,2-dimyristoyl-sn-glycero-3-phosphocholine (DMPC), which mimics cell membrane phospholipids, a truncated amphiphilic apolipoprotein E with a mass of 22 kD (Apo E422k) scaffold protein or an insect lipophorin, and cholate, a surfactant used to aid NLP self-assembly.

The mixture is expected to be thermally cycled above and below the transition temperature of DMPC to facilitate NLP self-assembly in accordance with the procedure described in US application "Nanolipoprotein particles comprising hydrogenase and related products methods and systems" Ser. No. 12/352,472, filed on Jan. 12, 2009.

In particular, Applicants expect entrapment of membrane associated rubber biosynthetic enzymes in NLP constructs. For instance, apolipoproteins and "helper" lipids are expected to be added to a collection of disrupted rubber particle (RPs) membranes. Therein, the biosynthetic enzymes associated with rubber biosynthesis would be incorporated into NLPs as they naturally self-assemble, creating nanoparticles that contain stabilized functional enzymes capable of rubber biosynthesis. Recapitulation of this natural process free of the entrapments and complexity of the plant super structure, (e.g. cellular and vascular components), is expected to allow production of high molecular weight rubber raw material free from contaminants normally found in rubber latex material harvested from a field environment.

In particular, an exemplified process is expected to be directed at removing the biosynthetic enzymatic "machinery" from the plant superstructure without impairing and possibly without affecting specific enzymatic activities and result in production of natural rubber or NR.

Example 6

Production of Immobilized Rubber Synthetic Enzyme/NLPs

Immobilized rubber synthetic enzyme/NLP were produced by associating RuT-NLPs to a support.

In particular, RuT-NLP assemblies were provided based on the observation that the NLP scaffold protein provides a handle for the eventual immobilization of the enzyme on surfaces for heterogeneous catalysis. Additionally, the presence of the scaffold protein constrains the dimensions of the bilayer and ensures quantized, controllable [16, 17] NLP particle size distributions which are stable and consistent between preparations compared to other model membrane systems, such as inverted vesicles and detergent micelles. For example, artificial vesicles are largely insoluble, and structurally unstable. Furthermore, because vesicles are spherical and therefore contain both an exposed and buried leaflet, a large fraction of the enzymes of interest will have active sites buried inside the vesicle.

Incorporation into lipid nanoparticles is expected to enable RuT to be immobilized on high surface area porous supports for continuous reactant cycling, and to be tested in a solution phase synthetic enzyme pathways for ex-vivo production from biomass.

Example 7

Hybrid Microbial Fuel Cell Using Bioinspired Molecular Nanolipoprotein Particles A prototype hydrogen production device that is based upon the in vitro reconstitution of hydrogen evolution in microbes has been designed by the Applicants and is depicted in the schematic illustration of FIG. 3. In particular the diagram of FIG. 3 shows possible design of a prototype rubber production mimetic device which is expected to be used to test/optimize biosynthetic enzymes and collect rubber polymer products for evaluation.

Example 8

Ex Vivo Production of Natural Rubber Using NLP-Stabilized Biosynthetic Enzymes In order to produce natural rubber, isolated rubber particles are subjected to breaking or shearing cells open by a sonicator or a vortex. In order to sonicate the cells without destroying the proteins through heat production by the sonicator, harvested cells are sonicated on a pulse system, using for example, a Misonix Q55 Sonicator w/ ⅛" probe, Ultrasonic Liquid Processor, Q55 with a setting at high level sonication at 8, 20 pulses at 0.5 seconds, for 3 cycles over ice. The rubber particles are then ultracentrifuged to remove the membrane bound particles from the cell debris.

The pellet containing the RuT complexes are then dissolved in buffer A (50 mM Tris HCl, pH 8.5, 100 mM NaCl, and 1 mM CHAPS detergent). After stirring for 1 hour in the detergent, the proteins are slowly dialyzed out to remove the CHAPS detergent, and concentrated using a centricon, and incorporated into NLPs, which are preformed NLP nanoconstructs. NiNLPs can also be used for this procedure. The NLPs or NiNLPs used for this procedure are fabricated using apolipoprotein A-I, and/or apolipoprotein E4, 22K, DMPC, DOPG, etc./The empty NLP integrity, i.e. size & shape, are determined by atomic force microscopy or AFM prior to use.

The empty NLPs are added to a buffered solution of active rubber transferase (RuT) derived from either: 1) recombinant cis-(1,4)-polyprenyl-transferase (CPT & His-tagged CPT) or 2) disrupted rubber particle membrane fragments as indicated above. The amount of RuT incorporated into NLP can then be determined by $C^{14}$-IPP incorporation assay an established industry-wide activity measurement test. Incubation is done with the NLPs at 4° overnight, followed by size exclusion chromatography to obtain pure NLPs with incorporated RuT.

The activity of the NLP stabilized NLPs are then tested using an $C^{14}$IPP incorporation assay. The process of rubber biosynthesis is monitored using an established assay that measures incorporation of radio-labeled isopreneyl-pyrophosphate or IPP. This assay provides a quantitative perspective on the overall biologically catalyzed polymerization reaction [43].

As shown in FIG. 4, several samples as controls were used to determine the activity levels of RuT purified from monolayer membranes and incorporated into bilayer NLPs. Samples that were tested included 1) washed rubber particle; 2) washed rubber particle with and EDTA control (which strips the cationic metal needed for the reaction); 3) NLP2 and WRP proteins incubated overnight; 4) NLP1 plus WRP proteins incubated overnight; 5) NLP1 plus WRP proteins incubated for 1 hour; 6) a buffer blank control; and 7) a $C^{14}$ IPP spike. As shown in the experimental $C^{14}$-IPP incorporation assay, NLP1 plus WRP proteins incubated for one hour had the largest amount of incorporation compared to the overnight incubations.

Example 9

Protocol for Cell Free Reactions

Preparative 1-ml reactions were carried out as described in Cappuccio et al 2008 [0049] using the Invitrogen Expressway Maxi kit or the Roche Applied Science RTS 500 ProteoMaster kit. In brief, lyophilized reaction components (lysate, reaction mixture, amino acid mixture, and methionine) were dissolved in Reconstitution Buffer and combined as specified by the manufacturer. For co-expression a total of 5 µg of plasmid DNA (RuT) was added to the lysate mixture along with added DMPC vesicles. The reactions were incubated at 22-25° C. according to the manufacturer's procedure for the different lysates for 4-18 h, typically overnight for large scale reactions (1 ml). For membrane protein survey studies, 0.2 µg of RuT encoding plasmid DNA and 1 µg of each membrane protein encoding plasmid DNA were added to the cell-free mixture where [35S]Met (135 mCi/mmol final concentration) (PerkinElmer Life Sciences) was added in place of methionine. The soluble fraction was obtained by centrifuging the completed reactions at 14,000 g for 5 min. Proteins were then separated by SDS-PAGE (data not shown). Autoradiograms and the percentage of solubility was determined using ImageJ software to quantize labeled protein. Protocols can be found in Cappucchio et al. [49]

Example 10

Purification of RuT-NLPs

The methods described below outlines nanolipoprotein Particle (NLP) formation and purification performed as described in Cappuccio et al 2008 [049]. The following materials and equipment were used: DMPC: 1,2-Dimyristoyl-sn-Glycero-3-Phosphocholine (Avanti Polar Lipids); Purified protein or truncation (RuT complex); TBS Buffer: 10 mM Tris-HCl; 0.15 M NaCl; 0.25 mM EDTA; 0.005% NaN3 (sodium azide); adjust to pH 7.4. 23.8° C. and 20° C. water baths; Probe or bath sonicator; Spin filter, 0.45 µm; Concentrator 50 kD MWCO, Vivaspin (Sartorius Inc.) (Other concentrator brands that are angled are also acceptable such as Agilent, because the nanolipoprotein particle produced will be larger than 200 kD, a 100 kD filter can be useful); FPLC Instrument (Shimadzu SCL—10A), size exclusion column (Superdex 200 10/300 GL (GE Healthcare Life Sciences).

Nanolipoprotein particles (NLPs) form in a self-assembly process in the correct mass ratio of apolipoprotein to lipid. This ratio needs to be optimized for each different apolipoprotein.

The water bath incubators were started with temperatures at 25° C. and 20° C. 34 mg of DMPC were probe sonicated into 1 mL of TBS at 6 amps for approximately 15 minutes or until optical clarity is achieved. DMPC solution was centrifuged at 13700 RCF for 2.5 min to remove residual metal from probe sonicator. The supernatant was transferred into a new tube. Apo E422K was combined with DMPC in a ratio of 1:4 by mass in TBS buffer in a 1.5 mL Eppendorf tube. Typically batches are of the 250 µL size.

Transition temperature procedure was performed as follows: the tube was immersed in water bath for 10 minutes each 25° C. (above DMPC transition temp.) followed by 20° C. (below DMPC transition temp.). The procedure was repeated three times then the tube was incubated at 23.8° C. overnight.

Filter preparation was performed through a 0.45 µm spin filter at 13700 RCF for 1 min and purify NLPs using size exclusion chromatography. A Shimadzu SCL-10A FPLC was used that was equipped with a Superdex 200 10/300 GL column with TBS buffer, a 200 µL sample injection volume, and a flow rate of 0.5 mL/min. Collect 0.5 mL fractions Fractions were concentrated using a Vivaspin 2 ultrafiltration device with a 50 MWCO.

These examples contain elements of fundamental biological processes that are expected to be separated from their respective cellular environments and re-cast in the acellular environment provided by NLPs. In the case of rubber, NLPs enable a transition from the tree to produce rubber to a stable molecular system/embodiment to produce rubber. In essence, NLPs enable removal of a biological process from the a whole entity, e.g. a cell, a plant an animal and re-cast said activity with just the germane molecular entities allowing more detailed investigation and understanding.

The examples set forth above are provided to give those of ordinary skill in the art a complete disclosure and description of how to make and use the embodiments of the NLPs, methods and systems of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed Thus, it should be understood that although the disclosure has been specifically disclosed by preferred embodiments, exemplary embodiments and optional features, modification and variation of the concepts herein disclosed can be resorted to by those skilled in the art, and that such modifications and variations are considered to be within the scope of this disclosure as defined by the appended claims It is to be understood that the disclosures are not limited to particular compositions or biological systems, which can, of course, vary. It is also to be understood that the terminology used herein is for the purpose of describing particular embodiments only, and is not intended to be limiting. It is also to be understood that the terminology used herein is for the purpose of describing particular embodiments only, and is not intended to be limiting. As used in this specification and the appended claims, the singular forms "a," an and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which is not specifically disclosed herein.

Although any methods and materials similar or equivalent to those described herein can be used in the practice for testing of the specific examples of appropriate materials and methods are described herein.

A number of embodiments of the disclosure have been described. The specific embodiments provided herein are examples of useful embodiments of the disclosure and it will be apparent to one skilled in the art that the disclosure can be carried out using a large number of variations of the devices, device components, methods steps set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims

REFERENCES

1. Goldet, G.; Wait, A. F.; Cracknell, J. A,; Vincent, K. A.; Ludwig, M.; Lenz, 0.; Friedrich, B.; Armstrong, F. A. *Journal of the American Chemical Society* 2008, 130, (33), 1 1106-1113.
2. Cracknell, J. A.; Vincent, K. A.; Ludwig, M.; Lenz, 0.; Friedrich, B.; Armstrong, F. A. *Journal of the American Chemical Society* 2007, 130, 424-425.
3. Kovacs, K. L.; Maroti, G.; Rakhely, G. *International Journal of Hydrogen Energy* 2006, 31, (1 I), 1460-1468.
4. Ho, D.; Chu, B.; Lee, H.; Brooks, E. K.; Kuo, K.; Montemagno, C. D. *Nanotechnology* 2005, 16, (12), 3120-3132.
5. Vincent, K. A.; Cracknell, J. A,; Lenz, 0.; Zebger, I.; Friederich, B.; Armstrong, F. *Proceedings of the National Academy of Sciences* 2005, 102, (47), 16951-16954.
6. Zhang, Y.-H. P.; Evans, B. R.; Mielenz, J. R.; Hopkins, R. C.; Adams, M. W. W. *PLoS ONE* 2007, e456, (S), 1-6.
7. Sanderson, K. *Nature* 2008, 452, 400-402.
8. Woodward, J.; Mattingly, S. M.; Danson, M.; Hough, D.; Ward, N.; Adams, M. *Nature Biotechnology* 1996, 14, 872-874.
9. Woodward, J.; Orr, M.; Cordray, K.; Greenbaum, E. *Nature* 2000, 405, 1014-1015.
10. Elgren, T. E.; Zadvorny, O. A.; Brecht, E.; Douglas, T.; Zorin, N. A,; Maroney, M. J.; Peters, *Nano Letters* 2005 Vol. 5, No. 10 2085-2087.
11. Sapra, R.; Bagratnyan, K.; Adams, M. W. W. *Proceedings of the National Academy of Sciences* 2003, 100, (13), 7545-7550.
12. Sapra, R.; Verhagcn, M. F. J. M.; Adams, M. W. W. *Journal of Bacteriology* 2000, 182, (12), 3423-3428.
13. Bayburt, T. H.; Grinkova, Y. V.; Sligar, S. G. *Nano Letters,:* 2002, 2, (8), 853-856
14. Bayburt, T. H.; Sligar, S. G. *Protein Science* 2003, 12, 2476-2481
15. Borch, J.; Torta, F.; Sligar, S. G.; Roepstostf, P. *Analytical Chemistry* 2008, 80, (16), 6245-6252.
16. Blanchette, C. D.; Law, R.; Benner, W. H.; Pesavento, J. B.; Cappuccio, J. A,; Walsworth, V. L.; Kuhn, E. A,; Corzette, M.; Chromy, B. A,; Segelke, B. W.; Coleman, M. A,; Bench, G.; Hoeprich, P. D.; Sulcheck, T. A. *Journal of Lipid Research* 2008, 49, (7), 1420-1430.
17. Chromy, B. A.; Arroyo, E.; Blanchette, C. D.; Bench, G.; Benner, H.; Cappuccio, J. A,; Coleman, M. A.; Henderson, P. T.; Hinz, A. K.; Kuhn, E. A.; Pesavento, J. B.; Segclke, B. W.; Sulcheck, T. A.; Tarasow, T.; Walsworth, V. L.; Hoeprich, P. D. *Journal of the American Chemical Society* 2007, 129, 14348-14354.
18. Nath, A,; Atkins, W. M.; Sligar, S. G. *Biochemistry* 2007, 46, (8), 2059-2069.
19. Boldog, T.; Grimme, S.; Li, M.; Sligar, S.; Hazelbauer, G. L. *Proceedings of the National Academy of Sciences* 2006, 103, (31), I 1509-1 1514.
20. Lenz, A. J.; Bayburt, T. H.; Basnakov, A. N.; Springer, B. A,; Sligar, S. G. *Biotechniques* 2006, 40, (5), 60 1-6 12.
21. Hedderich, R. *Journal of Bioenergetics and Biomembranes* 2004, 36, (I), 65-75
22. Vignais P M.; Billoud B. Ocurrence, Classification, and Biological Function of Hydrogenases: An overview. *Chemical Reviews* 2007, 107, 4206-4272.
23. Jed O. Eberly and Roger L. Ely *Critical Reviews in Microbiology,* 34:117-130, 2008
24. Sun, X. et al. Membrane-Mimetic Films of Aymmetric Phosphtidylcholine Lipid Bolaamphiphiles. *Langmuir* 2006, 22, 1201-1208

25.: Meyer, J. "Fe/Fe hydrogenases and their evolution: a genomic perspective." Cell. Mol. Life. Sci. 64 2007 1063-1084
26. Vincent, K. A. et al. "Investigating and Exploiting the Electrocatalytic Properties of Hydrogenases" Chem. Rev. 2007 107, 4366-4413.
27. Parkin, A., Goldet, G. Cavazza, C. Fontecilla-Camps, J., Armstrong, F. J. Am Chem. Soc. 2008, 13 (40) 13410-13416
28. K. Cornish & J. J. Blakeslee, "Rubber Biosynthesis in Plants", American Oil Chemist Society, The Lipid Library, Nov. 2, 2011
29. H-H. Greve, Ullman's Encyclopedia of Industrial Chemistry, Rubber, 2. Natural, 2012 Wiley-VCH Verlag GmbH & Co., KGaA, Weinheim, DOI: 10.1002/14356007.a23_225
30. G. Ponciano et al. "Transcriptome and gene expression analysis in cold-acclimated guayule (*Parthenium argentum*) rubber-producing tissue", (2012) Phytochemistry 79:57-66
31. S. Baker et al. "Hydrogen Production by a Hyperthermophilic Membrane-Bound Hydrogenase in Water Soluble Nanolipoprotein Particles" (2009), J. Amer. Chem. Soc., 131:7508-7509
32. C. Donniger & G. Popjak, "An Improved Synthesis of Isopentenyl Pyrophosphate" (1967) Biochem. J. 105:545-547
33. B. Chromy et al. "Different Apolipoproteins Impact Nanolipoprotein Particle Formation" (2007) J. Amer. Chem. Soc. 129:14384-14354
34. F. Katzen et al. "Insertion of Membrane Proteins into Discoidal Membranes using a Cell-free Protein Expression Approach (2008) J. Proteome Res.; ASAP Article; DOI: 10.1021/pr800265f
35 T. Schmidt et al. "Characterization of rubber particles and rubber chain elongation in *Taraxacum koksaghyz*." (2010) BMC Biochemistry 11:1-11
36. D. J. Siler et al. "Composition of rubber particles of *Hevea brasiliensis*, *Parthenium argentatum*, *Ficus elastics* and *Euphorbia lactiflua* indicates unconventional surface structure" (1997) Plant Physiol. Biochem. 35:881-889
37. Hiraishi, Tomohiro; Taguchi, Seiichi Mini-Reviews in Organic Chemistry, Volume 6, Number 1, February 2009, pp. 44-54(11) Bentham Science Publishers
38. N. Ohya; T. Koyama, (2001). "Biosynthesis of Natural Rubber and Other Natural Polyisoprenoids". Biopolymers Polyisoprenoids. 2 73-81.
39. J. C. Paterson-Jones, M. G. Gilliland, J. Van Staden, The Biosynthesis of Natural Rubber, Journal of Plant Physiology, Volume 136, Issue 3, June 1990, Pages 257-263.
40. Christian Schulze Gronover, Daniela Wahler and Dirk Prufer (2011). "Natural Rubber Biosynthesis and Physics—Chemical Studies on Plant Derived Latex, Biotechnology of Biopolymers" Magdy Elnashar (Ed.), ISBN: 978-953-307-179-4, InTech, Available from:
41 W. Xie; C. M. McMahan; A. J. DeGraw' M. D. Distefano; K. Cornish; M. C. Whalen; D. K. Shintani, "Initiation of rubber synthesis: In vitro comparisons of benzophenone-modified diphosphate analogues in three rubber preducing species", Phytochemistry 69 (2008) 2539-2545
42. P. J. Casey; M. C. Seabra, (1996). "Protein Prenyltransferases". Journal of Biological Chemistry 271 (10): 5289-5292
43. Plant Physio Biochem (1996) 34:334-377
44. Cornish, K. "Natural Rubber Biosynthesis in Plants: Rubber Transferase" Methods in Enzymology, (2012) Volume 515, pp. 64-80.
45. Singh et al in Journal of Experimental Botany Vol. 54, No. 384, pp. 985±992, March 2003
46. Whalen et al Chapter 23 of T. J. Bach and M. Rohmer (eds.), *Isoprenoid Synthesis in Plants and Microorganisms: New Concepts* 329 *and Experimental Approaches*, Springer Science+Business Media New York, 2013
47. Deborah J. Siler, Marta Goodrich-Tanrikulu, Katrina Cornish, Allan E. Stafford and Thomas A. McKeon *Plant Pliysiol. Biocliem.*, 1997, 35 (11), 881-889
48. Zhiqiang Pan, Francis Durst§, Daniele Werck-Reichhart§, Harold W. Gardner 11, Bilal Camarall, Katrina Cornish, and Ralph A. Backhausi The journal of Biological Chemistry, Vol. 270, No. 15, Issue of April 14, pp. 8487-8494, 1995
49. Cappucchio J. Molecular and Cellular Proteomics 7.11 (2008) pp. 2246-2253

What is claimed is:
1. A nanolipoprotein particle comprising
a target protein,
a membrane forming lipid, and
a scaffold protein,
wherein the target protein is a natural rubber transferase complex (RuT), wherein the natural rubber transferase complex is provided within a discoidal membrane lipid bilayer formed by the membrane forming lipid and stabilized by the scaffold protein, and wherein the membrane lipid bilayer is attached to the RuT through interaction of the natural rubber transferase complex hydrophobic region with the membrane lipid bilayer.
2. The nanolipoprotein particle of claim 1, wherein the natural rubber transferase complex is a collection of enzymes capable of catalyzing formation of natural polyisoprene rubber.
3. The nanolipoprotein particle of claim 1, wherein the natural rubber transferase complex, is an isolated or purified naturally occurring rubber transferase.
4. The nanolipoprotein particle of claim 1, wherein the nanolipoprotein particle is immobilized to a support.
5. The nanolipoprotein particle of claim 4, wherein the support is a solid support.
6. A method to perform rubber biosynthesis, the method comprising:
providing reagents for performing said rubber biosynthesis;
providing the nanolipoprotein particle of claim 1; and
contacting the reagents with the nanolipoprotein particle of claim 1 for time and under conditions to allow the reaction to occur, thus performing said rubber biosynthesis.
7. The method of claim 6, wherein the natural rubber transferase complex, is an isolated or purified naturally occurring rubber transferase.
8. The method of claim 6 wherein the nanolipoprotein particle of claim 1 is immobilized on a solid support.
9. The method of claim 6, wherein the rubber biosynthesis is directed to rubber production.
10. A system to perform a rubber biosynthesis, the system comprising:
one or more nanolipoprotein particles of claim 1; and
reagents for performing the rubber biosynthesis catalyzed by the natural rubber transferase complex,
wherein the one or more nanolipoprotein particles of claim 1 and the reagents can be contacted for a time and under condition to allow the rubber biosynthesis to occur.
11. The system of claim 10, wherein the natural rubber transferase complex, is an isolated or purified naturally occurring rubber transferase.

12. A device for performing a rubber biosynthesis, the device comprising:
- a substrate compartment, a catalyst compartment, and a product compartment, with the substrate compartment in communication with the product compartment through the catalyst compartment, wherein
- the catalyst compartment comprises the nanolipoprotein particle according to claim 1 arranged in a biosynthetic assembly; and
- the substrate compartment is configured to comprise monomers for the rubber biosynthesis catalyzed by the natural rubber transferase complex and to allow contact between said monomers and said natural rubber transferase complex.

13. The device of claim 12, wherein the nanolipoprotein particle is comprised in the catalyst compartment immobilized to a solid support.

14. The device of claim 12, further comprising a product compartment in communication with the catalyst compartment, the product compartment configured to comprise the product produced following the reaction of a substrate with the biocatalyst.

15. The device of claim 12, wherein the natural rubber transferase complex is an isolated or purified naturally occurring RuT.

* * * * *